(12) United States Patent
Shiota et al.

(10) Patent No.: US 9,480,695 B2
(45) Date of Patent: Nov. 1, 2016

(54) METHODS FOR INDUCING OREXIN NEURONS AND AGENT FOR TREATING NARCOLEPSY OR EATING DISORDER

(71) Applicant: THE UNIVERSITY OF TOKYO, Tokyo (JP)

(72) Inventors: Kunio Shiota, Tokyo (JP); Shintaro Yagi, Tokyo (JP); Koji Hayakawa, Tokyo (JP); Mitsuko Hirosawa-Takamori, Tokyo (JP); Daisuke Arai, Tokyo (JP); Keiji Hirabayashi, Tokyo (JP)

(73) Assignee: The University of Tokyo, Tokyo (JP)

( * ) Notice: Subject to any disclaimer, the term of this patent is extended or adjusted under 35 U.S.C. 154(b) by 10 days.

(21) Appl. No.: 14/224,730

(22) Filed: Mar. 25, 2014

(65) Prior Publication Data

US 2014/0349964 A1 Nov. 27, 2014

Related U.S. Application Data

(63) Continuation-in-part of application No. PCT/JP2012/075137, filed on Sep. 28, 2012.

(60) Provisional application No. 61/540,601, filed on Sep. 29, 2011.

(30) Foreign Application Priority Data

Mar. 25, 2013 (JP) ................. 2013-062298

(51) Int. Cl.
*A61K 31/7008* (2006.01)
*G01N 33/50* (2006.01)
*C12Q 1/68* (2006.01)
*C12N 5/0793* (2010.01)

(52) U.S. Cl.
CPC ......... *A61K 31/7008* (2013.01); *C12N 5/0619* (2013.01); *C12Q 1/6876* (2013.01); *G01N 33/5008* (2013.01); *G01N 33/5058* (2013.01); *G01N 33/5091* (2013.01); *C12N 2500/34* (2013.01); *C12N 2501/999* (2013.01); *C12N 2506/02* (2013.01); *C12N 2506/08* (2013.01); *C12N 2506/45* (2013.01); *C12Q 2600/136* (2013.01); *C12Q 2600/158* (2013.01)

(58) Field of Classification Search
CPC ............ A61K 31/7008; C12N 5/0619; C12N 2506/02; C12N 2501/999; C12N 2506/08; G01N 33/5058; C12Q 1/6876; C12Q 2600/158; C12Q 2600/136
USPC ........... 514/62; 435/29, 377; 506/10; 536/53
See application file for complete search history.

(56) References Cited

U.S. PATENT DOCUMENTS

| 6,274,568 | B1 | 8/2001 | Schnaar et al. |
| 6,294,520 | B1* | 9/2001 | Naito ............ A61K 8/44 514/1.2 |
| 8,987,232 | B2* | 3/2015 | Shiota ............ A61K 31/7008 514/62 |
| 2009/0068742 | A1 | 3/2009 | Yamanaka |
| 2009/0317444 | A1 | 12/2009 | Escaich Ferrer et al. |

FOREIGN PATENT DOCUMENTS

| EP | 2314671 A1 | 4/2011 |
| JP | 09-301874 A | 11/1997 |
| JP | 10-182685 A | 7/1998 |
| JP | 2001-078794 A | 3/2001 |
| JP | 2009-545299 A | 12/2009 |
| JP | 2011-178702 A | 9/2011 |
| WO | WO 00/07602 A1 | 2/2000 |
| WO | WO 2007/069666 A1 | 6/2007 |
| WO | WO 2008/014970 A1 | 2/2008 |
| WO | WO 2009/153180 A1 | 12/2009 |
| WO | WO 2010/027028 A1 | 3/2010 |

OTHER PUBLICATIONS

Csuk et al. A Short Synthesis of 2-Acetamido-2-deoxy-5-thio-D-glucose and -D-mannose from 5-Thio-D-glucal. J. Chem. Soc., Chem. Commun., 1986, pp. 343-344.*
Hayakawa et al., *J. Biol. Chem.*, 288(24): 17099-17110 (2013).
European Patent Office, Extended European Search Report in European Patent Application No. 12837508.6 (Apr. 21, 2015).
Chemelli et al., *Cell*, 98: 437-451 (Aug. 20, 1999).
Downs et al., *Neurobiology of Aging*, 28: 1286-1295 (2007).
Kessler et al., *Neuroscience*, 178: 82-88 (2011).
Lin et al., *Cell*, 98: 365-376 (1999).
Porkka-Heiskanen et al., *Neurobiology of Aging*, 25: 231-238 (2004).
Sampathkumar et al., *Nature Chemical Biology*, 2(3): 149-152 (2006).
Sawai et al., *Neuroscience Letters*, 468: 51-55 (2010).
Shukitt-Hale et al., *Neurobiology of Aging*, 25: 223-229 (2004).
Terao et al., *Neuroscience Letters*, 332: 190-194 (2002).
Thannickal et al., *Neuron*, 27: 469-474 (2000).
Toshinai et al., *Endocrinology*, 147(5): 2306-2314 (2006).
Tsujino et al., *Pharmacological Reviews*, 61(2): 162-176 (2009).

(Continued)

*Primary Examiner* — Clinton Brooks
*Assistant Examiner* — Yih-Horing Shiao
(74) *Attorney, Agent, or Firm* — Leydig, Voit & Mayer, Ltd.

(57) ABSTRACT

The invention provides a method for producing an orexin neuron by culturing a pluripotent stem cell or a neural progenitor cell in the presence of N-acetyl-D-mannosamine and optionally in the presence of at least one inhibitor selected from the group consisting of a Sirtuin 1 inhibitor and an O-linked β-N-acetylglucosamine transferase inhibitor. The invention also provides a therapeutic agent for narcolepsy or eating disorders, such as anorexia, containing N-acetyl-D-mannosamine, which is based on the induction of orexin neuron in vivo.

9 Claims, 9 Drawing Sheets

(56) References Cited

OTHER PUBLICATIONS

Yamamoto et al., *Brain Research Bulletin*, 51(6): 515-521 (2000).
Yamanaka et al., *Neuron*, 38(5): 701-713 (2003).
Zhang et al., *Brain Research*, 930: 206-211 (2002).
Zhang et al., *Peptides*, 26: 2590-2596 (2005).
Japanese Patent Office, International Search Report in International Patent Application No. PCT/JP2012/075137 (Dec. 25, 2012).
International Bureau of WIPO, Written Opinion in International Patent Application No. PCT/JP2012/075137 (Apr. 1, 2014).

\* cited by examiner

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial
<220> FEATURE:
<223> OTHER INFORMATION: Hcrt primer forward

<400> SEQUENCE: 1
ctccaggcac catgaacttt                                                    20

<210> SEQ ID NO 2
<211> LENGTH: 20
<212> TYPE: DNA
<213> ORGANISM: Artificial
<220> FEATURE:
<223> OTHER INFORMATION: Hcrt primer reverse

<400> SEQUENCE: 2
agttcgtaga gacggcagga                                                    20

<210> SEQ ID NO 3
<211> LENGTH: 22
<212> TYPE: DNA
<213> ORGANISM: Artificial
<220> FEATURE:
<223> OTHER INFORMATION: Actb primer forward

<400> SEQUENCE: 3
ttctacaatg agctgcgtgt gg                                                 22

<210> SEQ ID NO 4
<211> LENGTH: 20
<212> TYPE: DNA
<213> ORGANISM: Artificial
<220> FEATURE:
<223> OTHER INFORMATION: Actb primer reverse

<400> SEQUENCE: 4
atggctgggg tgttgaaggt                                                    20

<210> SEQ ID NO 5
<211> LENGTH: 25
<212> TYPE: DNA
<213> ORGANISM: Artificial
<220> FEATURE:
<223> OTHER INFORMATION: Actb primer forward

<400> SEQUENCE: 5
gacaacggct ccggcatgtg caaag                                              25

<210> SEQ ID NO 6
<211> LENGTH: 24
```

```
<212> TYPE: DNA
<213> ORGANISM: Artificial
<220> FEATURE:
<223> OTHER INFORMATION: Actb primer reverse

<400> SEQUENCE: 6
ttcacggttg gccttagggt tcag                                           24

<210> SEQ ID NO 7
<211> LENGTH: 20
<212> TYPE: DNA
<213> ORGANISM: Artificial
<220> FEATURE:
<223> OTHER INFORMATION: Prkcz primer forward

<400> SEQUENCE: 7
atgtctgctc ctccagcagt                                                20

<210> SEQ ID NO 8
<211> LENGTH: 20
<212> TYPE: DNA
<213> ORGANISM: Artificial
<220> FEATURE:
<223> OTHER INFORMATION: Prkcz primer reverse

<400> SEQUENCE: 8
atatcctttc gctgcactgg                                                20

<210> SEQ ID NO 9
<211> LENGTH: 311
<212> TYPE: DNA
<213> ORGANISM: Artificial
<220> FEATURE:
<223> OTHER INFORMATION: Probe

<400> SEQUENCE: 9
cgtgttcctg ccgtctctac gaactgttgc acggagctgg caaccacgct gcgggtatcc    60
tgactctggg aaagcggcgg cctggacctc caggcctcca gggacggctg cagcgcctcc   120
ttcaggccaa cggtaaccac gcagctggca tcctgaccat gggccgccgc gcaggcgcag   180
agctagagcc acatccctgc tctggtcgcg gctgtccgac cgtaactacc accgctttag   240
caccccgggg agggtccgga gtctgaaccc atcttctatc cttgtcctga tccaaacttc   300
cccctctgct c                                                        311
```

METHODS FOR INDUCING OREXIN NEURONS AND AGENT FOR TREATING NARCOLEPSY OR EATING DISORDER

CROSS-REFERENCE TO RELATED APPLICATIONS

This patent application is a continuation-in-part of International Patent Application No. PCT/JP2012/075137, filed on Sep. 28, 2012, which claims the benefit of U.S. Provisional Patent Application No. 61/540,601, filed Sep. 29, 2011, and Japanese Patent Application No. 062298/2013 filed on Mar. 25, 2013, which are incorporated by reference in their entireties herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 2,375 bytes ASCII (Text) file named "716464SequenceListing_ST25.txt" created Mar. 24, 2014.

TECHNICAL FIELD OF THE INVENTION

The present invention relates to a method for inducing an orexin neuron, more particularly, a method for efficiently producing an orexin neuron from a pluripotent stem cell or a neural progenitor cell. In addition, the present invention relates to a therapeutic agent of narcolepsy or an eating disorder, and to the field of treatment of diseases improved by orexin neuron regeneration.

Orexin is an intracerebral peptide which promotes wakefulness, and constitutes an orexin regulatory system and plays the central function of regulating wakefulness-sleep via an orexin receptor which is widely distributed in the brain (Non-Patent Document 1). Experimentally, lack of orexin leads to narcolepsy (a pathological condition in which a person suddenly and paroxysmally falls into short sleep) (Non-Patent Documents 2 and 3). Further, the concentration of orexin in the cerebrospinal fluid of a narcolepsy patient is as low as about ⅓ of that of a healthy person, and decrease in the number of orexin neurons is also observed. It has been revealed that the hypofunction of the orexin system influences on the wakefulness-sleep cycle, and also adversely influences on maintenance of homeostasis. The proper activity of the orexin system is essential for maintaining normal wakefulness-sleep and maintaining homeostasis (Non-Patent Document 4). For this reason, development of an orexin action promoter (agonist) or inhibitor (antagonist) has been attracting attention. On the other hand, when an orexin producing cell (orexin neuron) is absent or decreased, effectiveness of such agonists or antagonists is limited. However, until now, there is no report on successful methods to induce an orexin neuron in vivo or in vitro.

N-acetyl-D-mannosamine, an isomer of N-acetyl-D-glucosamine, is known as, for example, a starting material for the enzymatic synthesis of sialic acid (N-acetyl-neuraminic acid), which serves as a medicament and a starting material for other medicaments. Also, N-acetyl-D-mannosamine permits enzymatic synthesis of sialic acid derivatives from derivatives thereof, hence an industrially important substance. In a known method of producing N-acetyl-D-mannosamine, the molar conversion yield of N-acetyl-mannosamine from N-acetylglucosamine in isomerizing the latter under alkaline conditions is increased by the addition of boric acid or borate (patent reference 1). Another known method is such that sialic acid, as the substrate, is reacted with N-acetyl-neuraminate lyase to produce N-acetyl-D-mannosamine (patent reference 2). A method has been proposed wherein the acylated form of N-mannosamine is contacted with cells to regulate lectin binding to cell surfaces or to regulate the proliferation of nerve cells (patent reference 3).

The present inventors have found that N-acetyl-D-mannosamine is effective in ameliorating brain hypofunction and in ameliorating sleep disorders (patent documents 4 and 5).

DOCUMENT LIST

Patent Documents

[patent document 1] JP-A-HEI10-182685
[patent document 2] JP-A-2001-78794
[patent document 3] U.S. Pat. No. 6,274,568
[patent document 4] WO2010/027028
[patent document 5] JP-A-2011-178702

Non-Patent Documents

[non-patent document 1] Pharmacological Reviews 61:162-176, 2009
[non-patent document 2] Cell 98: 365-376, 1999
[non-patent document 3] Cell 98: 437-451, 1999
[non-patent document 4] Neuroscience 178: 82-88, 2011

SUMMARY OF THE INVENTION

Problems to be Solved by the Invention

Destabilization of wakefulness-sleep causes a serious brain dysfunction such as reduction in cognitive or learning capacity, and leads to deterioration in the brain function. Previously, induction of sleep has been tried by a sleep-inducing drug aiming at improvement in sleep. The orexin action promoter or inhibitor is an extension thereof. However, particularly, the problem of wakefulness-sleep accompanied with aging is a problem of reduction in the quality of sleep or destabilization of wakefulness-sleep rather than decrease in the sleeping time. The orexin system is essential for stabilization of wakefulness-sleep. When it becomes possible to induce an orexin neuron, this provides a new treatment method covering diseases exhibiting abnormality of the wakefulness-sleep cycle. An object of the present invention is to provide a means for inducing an orexin neuron in vitro.

It is said that 0.2% of the world's population suffers from narcolepsy. Experimentally, absence of orexin gene or a receptor gene thereof causes narcolepsy symptoms; however, mutation or absence of orexin gene or a receptor gene thereof is rarely seen in the patients. There is no basic therapy for narcolepsy, and treatment is performed with psychic energizer (methylphenidate (Ritalin), Pemoline (Betanamin), Modafinil (Modiodal) etc.), as well as psychotropic drugs and anesthetics. However, they are associated with the problem of drug dependency. The etiology of narcolepsy is a decrease or lack of orexin-producing cells. Therefore, the development of a basic therapeutic drug for narcolepsy is desired, and an object of the present invention is to provide a basic therapeutic drug for narcolepsy.

Means of Solving the Problems

The present inventors extensively investigated to solve the above-described problems and, as a result, found out that by adding N-acetyl-D-mannosamine, or a combination of N-acetyl-D-mannosamine with a particular inhibitor to a medium during the process of differentiation into a nerve cell, an orexin neuron can be induced from a pluripotent stem cell or a neural progenitor cell, resulting in completion of the present invention.

In addition, the present inventors considered it necessary to prevent a decrease in orexin cells or an increase in orexin cells for the treatment or prophylaxis of narcolepsy, and conducted intensive studies. As a result, they have found that administration of N-acetyl-D-mannosamine to an animal unexpectedly increases the cells that express orexin gene in the lateral hypothalamic area, which resulted in the completion of the present invention.

That is, the present invention is as follows.

[1] A method for producing an orexin neuron, comprising a step of culturing a pluripotent stem cell or a neural progenitor cell in the presence of N-acetyl-D-mannosamine.
[2] The method according to [1], wherein the pluripotent stem cell is an embryonic stem cell, a somatic stem cell or an induced pluripotent stem cell.
[3] The method according to [1], wherein the neural progenitor cell is a fetus-derived neurosphere.
[4] An orexin neuron, which is obtainable by the method according to any of [1] to [3].
[5] A method for screening for a drug which acts on regulation of wakefulness-sleep, comprising using the orexin neuron according to [4].
[6] The screening method according to [5], wherein the drug is a therapeutic agent for narcolepsy.
[7] A method for inducing an orexin neuron, comprising a step of administering an effective amount of N-acetyl-D-mannosamine to a subject in need thereof, or having an effective amount of N-acetyl-D-mannosamine taken by a subject in need thereof.
[8] An agent for inducing an orexin neuron from a neural progenitor cell or a nerve cell, comprising N-acetyl-D-mannosamine as an active ingredient.
[9] A method for producing an orexin neuron, comprising a step of culturing a pluripotent stem cell or a neural progenitor cell in the presence of N-acetyl-D-mannosamine, and at least one inhibitor selected from the group consisting of a Sirtuin (Sirt) inhibitor and an O-linked β-N-acetylglucosamine transferase (OGT) inhibitor.
[10] The method according to [9], wherein the pluripotent stem cell is an embryonic stem cell, a somatic stem cell or an induced pluripotent stem cell.
[11] The method according to [9], wherein the neural progenitor cell is a fetus-derived neurosphere.
[12] An orexin neuron, which is obtainable by the method according to any of [9] to [11].
[13] A method for screening for a drug which acts on regulation of wakefulness-sleep, comprising using the orexin neuron according to [12].
[14] The screening method according to [13], wherein the drug is a therapeutic agent for narcolepsy.
[15] A kit for inducing an orexin neuron from a neural progenitor cell or a nerve cell, comprising, as active ingredients, N-acetyl-D-mannosamine, and at least one kind of inhibitor selected from the group consisting of a Sirtuin 1 (Sirt1) inhibitor and an O-linked β-N-acetylglucosamine transferase (OGT) inhibitor, which are contained in separate vessels.
[16] A method for treating narcolepsy or eating disorder based on induction of orexin neuron in vivo, comprising a step of administering an effective amount of N-acetyl-D-mannosamine to a subject in need thereof.
[17] The method of [16], wherein orexin neuron is induced in the lateral hypothalamic area.
[18] The method of [16] or [17], wherein the eating disorder is anorexia.

Effect of the Invention

The present inventors first demonstrated that addition of ManNAc (including a derivative, a precursor or a prodrug thereof) or a combination of ManNAc and a Sirt inhibitor and/or an Ogt (O-linked β-N-acetylglucosamine (O-GlcNAc) transferase) inhibitor has the action of inducing an orexin neuron in a culture system of a pluripotent stem cell including an ES cell, or a neural progenitor cell.

ManNAc (including a derivative, a precursor or a prodrug thereof) or a combination of ManNAc and a Sirt inhibitor and/or an Ogt inhibitor is effective for diseases exhibiting symptoms due to decrease or lack of an orexin neuron. An orexin neuron produced using ManNAc (including a derivative, a precursor or a prodrug thereof) or a combination of ManNAc and a Sirt inhibitor and/or an Ogt inhibitor can provide a new drug therapy or drug screening. The present invention can also contribute to regeneration medicine aiming at recovery of an orexin neuron.

N-acetyl-D-mannosamine is effective for narcolepsy showing symptoms caused by a decrease or lack of orexin neurons, and is highly safe. Using N-acetyl-D-mannosamine, a decrease in orexin neurons can be prevented, or contribution can be made to the medical care aiming at recovery. Since administration of N-acetyl-D-mannosamine also induces production of orexin, which was originally found as a neuropeptide relating to the control of appetite, N-acetyl-D-mannosamine is also useful as a therapeutic drug for eating disorder.

DESCRIPTION OF EMBODIMENTS

Figure 1:
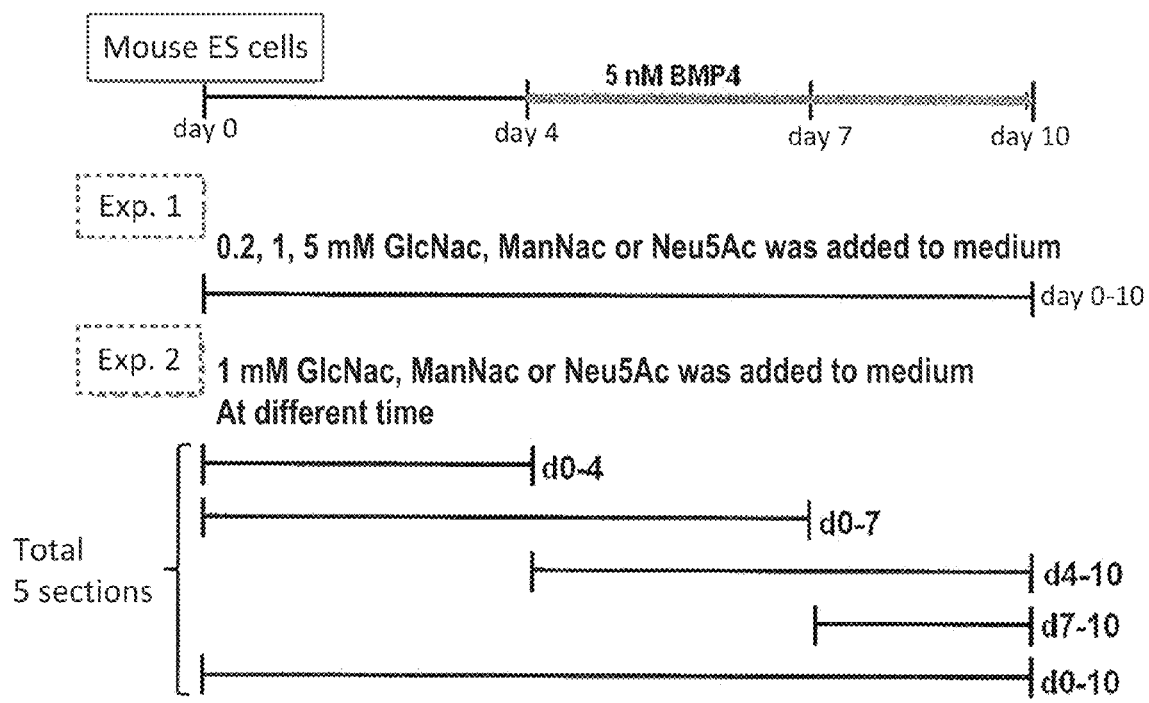
FIG. 1 shows a schedule of induction of neural differentiation from a mouse ES cell using a SDIA differentiation culture system.

In the present invention, an orexin neuron refers to a nerve cell which expresses an orexin (hypocretin: Hcrt) gene. The orexin neuron is mainly distributed in the lateral nucleus of hypothalamus in vivo. The orexin neuron is differentiation-induced from a pluripotent stem cell or a neural progenitor cell in vitro by the production method of the present invention described later. Whether a nerve cell is the orexin neuron or not can be confirmed by investigating and identifying the presence or absence of expression of a Hcrt gene in the cell by a known procedure such as a PCR method, in situ hybridization, immunological detection using an antibody (immunostaining, Western blotting, enzyme immunoassay (ELISA)), or further detection of a reaction of the neuron on various stimulations.

Regarding Hcrt, an mRNA and a protein of human Hcrt are published as NCBI Reference Sequence: NM_001524.1, and an mRNA and a protein of mouse Hcrt are published as NCBI Reference Sequence: NM_010410.2.

In the present invention, N-acetyl-D-mannosamine may be an N-acetyl form of D-mannosamine represented by the following formula (I):

(I)

A compound represented by the formula (I) is abbreviated as "ManNAc" in some cases.

In the present invention, N-acetyl-D-mannosamine is not limited to a simple substance represented by the formula (I), and is a concept including a derivative, a precursor or a prodrug thereof, a salt thereof, and a solvate thereof (hereinafter, referred to as "the derivative of the present invention, etc." in some cases).

N-acetyl-D-mannosamine may be, for example, a compound represented by the following formula (II):

(II)

[wherein each of $R^1$, $R^2$, $R^3$, $R^4$ and $R^5$ independently represents hydrogen (H), $R^6$, —C(=O) $R^6$, —C(=O)O$R^6$, or —C(=O) N$R^6R^7$; $R^6$ represents an optionally substituted $C_1$-$C_7$ linear or cyclic hydrocarbon; $R^7$ represents hydrogen (H), or an optionally substituted $C_1$-$C_7$ linear or cyclic hydrocarbon.]

Useful substituents are F, Cl and Br.

In addition, the above-mentioned formula (II) may also be an embodiment mentioned below.

[wherein $R^1$, $R^2$, $R^3$ and $R^4$ each independently represents hydrogen (H), $R^6$, —C(=O) $R^6$, —C(=O)O$R^6$, or —C(=O) N$R^6R^7$, $R^6$ represents $C_{1-7}$ linear hydrocarbon optionally having substituent(s) or cyclic hydrocarbon, $R^7$ represents hydrogen (H), or $C_{1-7}$ linear hydrocarbon or cyclic hydrocarbon optionally having substituent(s).

$R^5$ represents hydrogen (H), $R^6$, —C(=O)O$R^6$, —C(=O) N$R^6R^7$ or —C(=O)—CH$_2$—$R^8$, $R^6$ represents $C_{1-7}$ linear hydrocarbon or cyclic hydrocarbon optionally having substituent(s), $R^7$ represents hydrogen (H), $C_{1-7}$ linear hydrocarbon or cyclic hydrocarbon optionally having substituent(s), $R^8$ represents $C_{1-7}$ linear hydrocarbon or cyclic hydrocarbon optionally having substituent(s), —(CH$_2$)$_n$—C(=O)$R^9$ (n is an integer of 1-6 and $R^9$ is $C_{1-6}$ alkyl), —NH—C(=O)$R^{10}$ ($R^{10}$ is $C_{1-7}$ linear hydrocarbon optionally having substituent(s)), azido, oxycarbonyl-$C_{1-6}$ alkyl, or thiocarbonyl-$C_{1-6}$ alkyl]

As the substituent, a halogen atom (fluorine, chlorine, bromine, iodine) can be used.

N-Acetyl-D-mannosamine may be compounds represented by, for example, the following formulas (IIa)-(IIc) and (IIIa)-(IIIc).

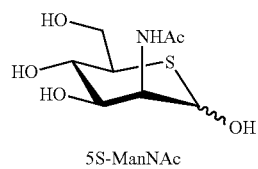

5S-ManNAc (IIa)

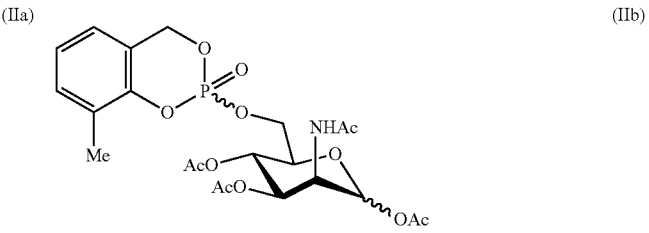

Ac$_3$ManNAc-6csP (IIb)

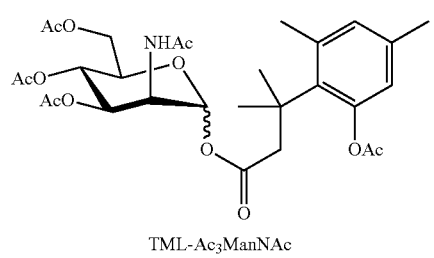

TML-Ac$_3$ManNAc (IIc)

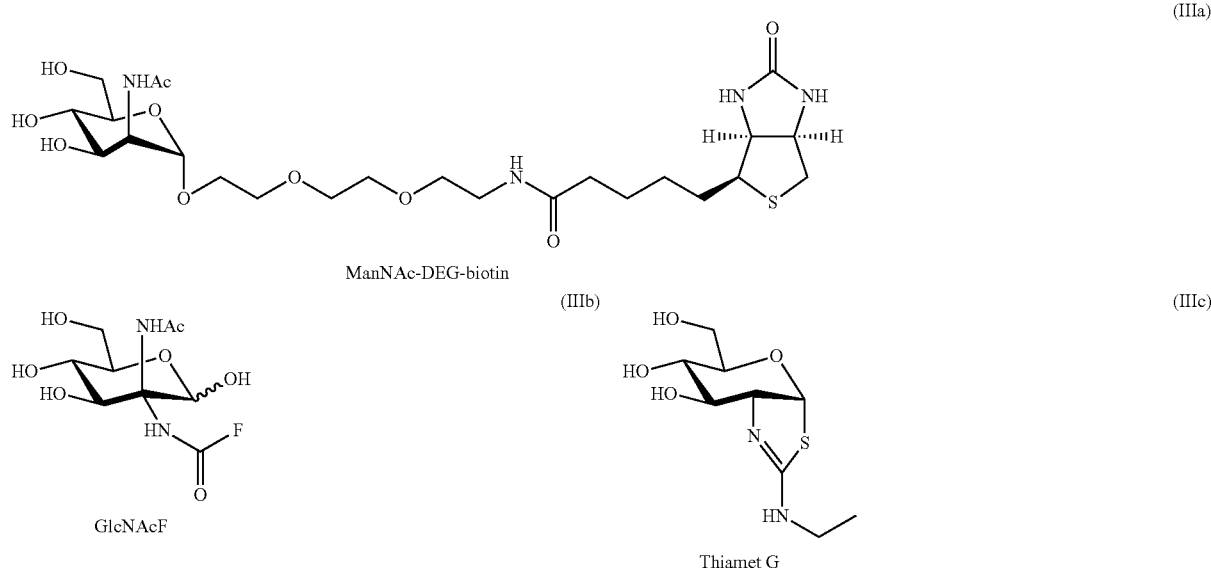

The derivative and the like of the present invention are also described in documents (Metabolic glycoengineering: Sialic acid and beyond Glycobiology 2009 vol. 19 (12) pp. 1382-1401 (particularly FIG. 4), Metabolic oligosaccharide engineering with N-Acyl functionalized ManNAc analogs: Cytotoxicity, metabolic flux, and glycan-display considerations Biotechnol Bioeng 2011 vol. 109 (4) pp. 992-1006 (particularly FIG. 2)), and can also be used preferably in the present invention.

Salts of N-acetyl-D-mannosamine include pharmacologically acceptable salts, for example, salts with inorganic acids, salts with organic acids, and salts with basic or acidic amino acids.

Examples of the salts with inorganic acids include salts with hydrochloric acid, hydrobromic acid, nitric acid, sulfuric acid, and phosphoric acid.

Examples of the salts with organic acids include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

Examples of the salts with basic amino acids include salts with arginine, lysine and ornithine, and examples of the salts with acidic amino acids include salts with aspartic acid and glutamic acid.

Preferred examples of the solvate include hydrates (e.g., monohydrates and dihydrates) and ethanolate.

The N-acetyl-D-mannosamine used may be, a commercially available product, or may be produced by a method known per se. Examples of a method for producing N-acetyl-D-mannosamine represented by the formula (I) include, but are not limited to, a method involving isomerizing N-acetylglucosamine under an alkaline condition (JP-A-HEI-10-182685) and a method involving a reaction of sialic acid as the substrate with N-acetylneuraminic acid lyase (JP-A-2001-78794). The derivative etc. of N-acetyl-D-mannosamine can also be produced by a method known per se using N-acetyl-D-mannosamine represented by the formula (I) as a raw material.

In the present invention, a "Sirtuin inhibitor" refers to a substance which inhibits expression or the activity of Sirtuin (a protein family including Sirt1 to 7). Sirtuin is a factor for regulating metabolism or aging, and Sirt1 to 3, 5 and 6 are known as a deacetylase of a protein including histone (Nature Reviews Molecular Cell Biology, 13, 225-238 (2012)). Examples of the Sirtuin inhibitor include, but are not limited to, a siRNA, a shRNA, an antisense RNA, and an antisense DNA which specifically inhibit expression of a Sirtuin gene, and a low-molecular weight compound which inhibits the activity of a protein deacetylase. Examples of a suitable Sirtuin inhibitor include 6-chloro-2,3,4,9-tetrahydro-1H-carbazole-1-carboxamide (EX-527: SIGMA-ALDRICH) commercially available as a Sirt1 inhibitor.

In the present invention, an "O-linked β-N-acetylglucosamine (O-GlcNAc) transferase inhibitor" refers to a substance which inhibits expression or the activity of O-linked β-N-acetylglucosamine transferase (Ogt). Ogt is an enzyme which catalyzes addition of N-acetylglucosamine to a hydroxy group of serine or threonine (Nature Reviews Cancer, 11, 678-684 (2011)). Examples of the Ogt inhibitor include, but are not limited to, a siRNA which specifically inhibits expression of an Ogt gene and a low-molecular weight compound which inhibits the N-acetylglucosamine addition activity. Examples of a suitable Ogt inhibitor include commercially available benzyl 2-acetamide-2-deoxy-α-D-galactopyranoside (BADGP: SIGMA-ALDRICH).

<Method for Producing Orexin Neuron>

The present invention provides a method for producing an orexin neuron comprising a step of culturing a pluripotent stem cell or a neural progenitor cell in the presence of N-acetyl-D-mannosamine.

The present invention also provides a method for producing an orexin neuron comprising a step of culturing a pluripotent stem cell or a neural progenitor cell in the presence of N-acetyl-D-mannosamine, and at least one inhibitor selected from the group consisting of a Sirt inhibitor and an Ogt inhibitor.

In the present invention, a "pluripotent stem cell" refers to an undifferentiated cell having a "self-regenerating ability" that it can proliferate while maintaining the undifferentiated state and a "differentiation pluripotency" that it can be differentiated into all or a part of triploblastic systems, particularly a nerve cell. Examples of the pluripotent stem cell include an embryonic stem (ES) cell, a primordial germ stem (EG) cell, a multipotent germ cell (mGS); a somatic stem cell such as a neural stem cell isolated from an adult or fetal brain, a mesenchymal stem cell isolated from bone marrow, blood or an adult tissue, a stromal cell, a fibroblast; and an induced pluripotent stem (iPS) cell.

In the present invention, a "neural progenitor cell" refers to a cell which underwent decision of differentiation into a nerve cell from the "pluripotent stem cell" via a neural progenitor cell formation stage. The neural progenitor cell can be obtained as a fetus-derived neurosphere. Alternatively, the neural progenitor cell can be obtained by culturing a differentiation pluripotent stem cell under a suitable neural differentiation condition, or dedifferentiating a somatic cell by a suitable method, and culturing this under the neural differentiation condition.

The cell that is a subject of the present invention is derived from a mammal such as mouse, rat, pig, rabbit, cat, dog, cow, horse, monkey or human, preferably mouse or human.

More specifically, examples of the embryonic stem cell used in the method of the present invention include an embryonic stem cell of a mammal which is established by culturing an early embryo before implantation (hereinafter, abbreviated as "embryonic stem cell I"), an embryonic stem cell which is established by culturing an early embryo made by transplanting a nucleus of a somatic cell (hereinafter, abbreviated as "embryonic stem cell II"), and an embryonic stem cell in which a gene on a chromosome of an embryonic stem cell of an embryonic stem cell I or II is modified using a genetic engineering technique (hereinafter, abbreviated as "embryonic stem cell III").

More specifically, examples of the embryonic stem cell I include an embryonic stem cell which is established from an inner cell mass constituting an early embryo, an EG cell which is established from a primordial germ cell, a cell isolated from a cell population (e.g. primitive ectoderm) having the multipotency of an early embryo before implantation, and a cell obtained by culturing the cell.

The embryonic stem cell I can be prepared by culturing an early embryo before implantation according to the method described in the literature (Manipulating the Mouse Embryo A Laboratory Manual, Second Edition, Cold Spring Harbor Laboratory Press (1994)).

The embryonic stem cell II can be made using, for example, the method reported by Wilmut et al. (Nature, 385, 810 (1997)), Cibelli et al. (Science, 280, 1256 (1998)), Akira IRITANI et al. (protein nucleic acid enzyme, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000)) and the like, as follows.

Development is initiated by using a method of removing a nucleus of a mammalian cell, reprogramming the nucleus (operation of returning the nucleus into a state where development can be repeated again) and injecting the nucleus into an enucleated unfertilized egg of a mammal. By culturing the egg which has initiated development, an egg having a nucleus of another somatic cell which has initiated normal development is obtained.

As a method of reprogramming a nucleus of a somatic cell, a plurality of methods are known. Reprogramming can be performed by inducing a cell cycle into a resting phase state (G0 phase or G1 phase) by, for example, conducting culturing by changing, as a medium in which a cell donating a nucleus is cultured, from a medium containing 5 to 30%, preferably 10% bovine fetal serum (e.g. M2 medium) to an oligotrophic medium containing 0 to 1%, preferably 0.5% bovine fetal serum for 3 to 10 days, preferably for 5 days.

Alternatively, reprogramming can be performed by injecting a nucleus of a cell donating a nucleus into an enucleated unfertilized egg of the same species of a mammal, and culturing the egg for a few hours, preferably for about 1 to 6 hours.

The reprogrammed nucleus can initiate development in an enucleated unfertilized egg. As a method of initiating development of an initialized nucleus in an enucleated unfertilized egg, a plurality of methods are known. By transplanting a nucleus, which has been reprogrammed by inducing a cell cycle into a resting phase state (G0 phase or G1 phase), into an enucleated unfertilized egg of the same species of a mammal by an electrofusion method or the like, an ovum can be activated to initiate development.

Development can be initiated by transplanting a nucleus, which has been reprogrammed by injecting a nucleus into an enucleated unfertilized egg of the same species of a mammal, into an enucleated unfertilized egg of the same species of a mammal again by a method using a micromanipulator or the like, stimulating the ovum with an ovum activating substance (e.g. strontium), and treating the ovum with an inhibitory substance of cell division (e.g. cytochalasin B) to inhibit release of a second polar body. This method is suitable for the case where the mammal is mouse or the like, for example.

Once an egg which has initiated development is obtained, an embryonic stem cell can be obtained using a known method described in, for example, Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Making of Mutant Mouse using ES Cell, Yodosha Co., Ltd. (1995).

The embryonic stem cell III can be made by, for example, using a homologous recombination technique. Examples of a gene on a chromosome to be modified upon preparation of the embryonic stem cell III include a gene of a histocompatibility antigen and a gene associated with a disease based on a disorder of a neural cell. Modification of a target gene on a chromosome can be performed using the method described in, for example, Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Making of Mutant Mouse using ES Cell, Yodosha Co., Ltd. (1995).

Specifically, for example, a genome gene of a target gene to be modified (e.g. a gene of a histocompatibility antigen or a disease-associated gene) is isolated, and the isolated genome gene is used to make a target vector for homologously recombining a target gene. The obtained target vector is introduced into an embryonic stem cell, and a cell which has caused homologous recombination between the target gene and the target vector is selected, thereby, an embryonic stem cell in which a gene on a chromosome has been modified can be made.

The embryonic stem cell can be obtained from prescribed institutions, or a commercially available product can also be purchased. For example, KhES-1, KhES-2 and KhES-3 which are human embryonic stem cells can be obtained from Institute for Frontier Medical Sciences, Kyoto University.

In the present invention, a "somatic stem cell" refers to an undifferentiated cell having the "differentiation pluripotency" that it can be differentiated into a neural cell of an ectoderm lineage, and is not derived from a germ cell. Examples of the somatic stem cell include a neural stem cell, a mesenchymal stem cell, a stromal cell, a fibroblast, and an adipocyte progenitor cell.

Mouse and human induced pluripotent stem cells (iPS cells) can be established according to WO 2004/092357 and WO 2007/069666. Alternatively, it is also possible to make an iPS cell by three factors except for a c-Myc gene (representative examples of which are Oct3/4, Klf4, and Sox2) (Takahashi, K. and Yamanaka, S., Cell, 126: 663-676 (2006)), or to induce an iPS cell using a plasmid or episomal vector without incorporation of an reprogramming factor into a genome (Okita, K. et al., Science, 322: 949-953 (2008); Yu, J. et al., Science, 324: 797-801 (2009)). The iPS cell can be established from, for example, a somatic cell such as a skin fibroblast according to the method described in the above literature.

The iPS cell can be obtained from prescribed institutions. For example, a 201B7 strain which is a human iPS cell can be obtained from Riken BioResource Center, RIKEN, Japan.

It is desirable to use, as the neural progenitor cell, a fetus-derived neural mass (derived from an endbrain, also referred to as neurosphere). In the case of a mouse fetus, it is desirable to remove the endbrain at an embryonic age of 14.5 days. Culture of the neural progenitor cell can be performed in accordance with the method described in Ciccolini F, Svendsen C N. Fibroblast growth factor 2 (FGF-2) promotes acquisition of epidermal growth factor (EGF) responsiveness in mouse striatal progenitor cells: identification of neural progenitors responding to both EGF and FGF-2. (1998), J Neurosci. 18(19): 7869-80, and a detailed culture method is described in Examples described later.

A medium used in the production method of the present invention can be prepared using, as a basal medium, a medium which is used in culture of an animal cell. The basal medium is not particularly limited as far as it is a medium which can be used in culture of an animal cell, such as a BME medium, a BGJb medium, a CMRL 1066 medium, a Glasgow MEM medium, an Improved MEM Zinc Option medium, an IMDM medium, a Medium 199 medium, an Eagle MEM medium, an αMEM medium, a DMEM medium, a DMEM/F12 medium, a Ham medium, a RPMI 1640 medium, a Fischer's medium, and a mixed medium of them.

The medium used in the production method of the present invention can be a serum-containing medium or a serum-free medium. Herein, the serum-free medium means a medium not containing non-adjusted or unpurified serum, and a medium containing a purified blood-derived component or an animal tissue-derived component (e.g. growth factor) corresponds to the serum-free medium. Examples of such a serum-free medium include a serum-free medium to which an appropriate amount (e.g. 1 to 20%) of commercially available KNOCKOUT™ SR (KSR) has been added, a serum-free medium to which insulin and transferrin have been added (e.g. CHO-S-SFM II (manufactured by GIBCO BRL), Hybridoma-SFM (manufactured by GIBCO BRL), eRDF Dry Powered Media (manufactured by GIBCO BRL), UltraCULTURE™ (manufactured by BioWhittaker), UltraDOMA™ (manufactured by BioWhittaker), UltraCHO™ (manufactured by BioWhittaker), UltraMDCK™ (manufactured by BioWhittaker), an ITPSG medium (Cytotechnology, 5, S17 (1991)), an ITSFn medium (Proc. Natl. Acad. Sci. USA, 77, 457 (1980)), and an mN3 medium (Mech. Dev. 59, 89 (1996)), and a medium to which a factor derived from a cell has been added (e.g. a medium to which the culture supernatant of a pluripotent teratocarcinoma cell PSA1 has been added (Proc. Natl. Acad. Sci. USA, 78, 7634 (1981)).

Furthermore, the medium used in the production method of the present invention may optionally contain other components, for example, an amino acid, pyruvic acid, 2-mercaptoethanol, a cytokine, and a growth factor in an appropriate concentration.

A culture vessel used in a culturing step of the production method of the present invention is not particularly limited as far as it is intended for cell culturing, and examples thereof include a flask, a flask for tissue culturing, a dish, a petri dish, a dish for tissue culturing, a multidish, a microplate, a microwell plate, a multiplate, a multiwell plate, a chamber slide, a schale, a tube, a tray, a culturing bag, and a roller bottle.

A medium and a culture vessel are appropriately selected from the aforementioned media and culture vessels according to the kind of the cell and an object, and culture of a pluripotent stem cell or a neural progenitor cell embryonic stem cell is initiated under a condition where the cell is differentiated into a nerve cell in vitro. Examples of a general culturing condition include a method of culturing for around 1 to 20 days in an incubator aerated with 2 to 10% $CO_2$ at 32 to 40° C.

In the case of addition of N-acetyl-D-mannosamine alone, it can be added to a medium from the starting day of culture (0th day of differentiation) until completion of culturing. Alternatively, an orexin neuron can also be induced by adding N-acetyl-D-mannosamine on 4th to 7th day of differentiation.

In the case of combined addition of N-acetyl-D-mannosamine and at least one inhibitor selected from the group consisting of a Sirt inhibitor and an Ogt inhibitor, N-acetyl-D-mannosamine can be added to a medium from the starting day of culture (0th day of differentiation) until completion of culturing. Alternatively, N-acetyl-D-mannosamine can also be added to a medium on 4th to 7th day of differentiation. The Sirt inhibitor and/or the Ogt inhibitor may be added from the 0th day of differentiation, but a protocol of adding the inhibitor to a medium on 4th to 7th day of differentiation is recommended.

It is recommended that the concentration of N-acetyl-D-mannosamine in a medium is 0.001 to 5 mM, preferably 0.01 to 1 mM. The concentration of the Sirt inhibitor in a medium is appropriately determined according to the kind of the inhibitor, and when EX-527 is used, 1 to 200 nM, preferably 5 to 50 nM is recommended. The concentration of the Ogt inhibitor in a medium is appropriately determined according to the kind of the inhibitor, and when BADGP is used, 1 to 50 mM, preferably 2 to 10 mM is recommended.

In the production method of the present invention, in order to more improve the efficiency of differentiation from a pluripotent stem cell or a neural progenitor cell into a neural cell, a known substance inducing differentiation into a neural cell can be used together. Examples of such a differentiation inducing substance include NGF, BDNF, NT3, retinoic acid, FGF, a BMP inhibiting factor, IGF and CNTF. The concentration of the differentiation inducing substance in a medium is appropriately determined according to the kind of the differentiation inducing substance.

In one embodiment, differentiation into an orexin neuron is induced by pre-culturing a stem cell or a progenitor cell for 4 to 7 days and, thereafter, adding N-acetyl-D-mannosamine alone to a medium in the presence of the substance inducing differentiation into a neural cell, if necessary.

In another embodiment, differentiation induction into an orexin neuron is enhanced by adding N-acetyl-D-mannosamine to a medium on the day when culture of a stem cell or a progenitor cell is initiated (0th day), and thereafter, adding at least one inhibitor selected from the group consisting of a Sirt inhibitor and an Ogt inhibitor to the medium on 4th to 7th days.

By the production method of the present invention, an orexin neuron can be efficiently induced in vitro, and a cultured orexin neuron can be provided.

<Screening Method>

The present invention provides a method for screening for a drug which acts on regulation of wakefulness-sleep, using an orexin neuron obtainable by the production method of the present invention.

In the screening method of the present invention, culture of the orexin neuron obtained as described above is continued under a condition where the orexin neuron is alive in vitro, a test substance is added to a medium, and proliferation of the orexin neuron is observed for a prescribed term.

Herein, the test substance may be any known substance and novel substance, and examples thereof include a nucleic acid, a saccharide, a fat, a protein, a peptide, an organic low-molecular weight compound, a compound library made using a combinatorial chemistry technique, a random peptide library made by solid phase synthesis or a phage display method, and a natural component derived from a microorganism, an animal, a plant, a marine organism or the like.

A method of culturing (maintaining) the orexin neuron in vitro is as described above in the production method of the present invention. In the present step, it is desirable to use a medium free of N-acetyl-D-mannosamine, a Sirt inhibitor and an Ogt inhibitor.

The presence or absence of proliferation of the orexin neuron can be confirmed by investigating the number and the distribution state of orexin neurons in a test substance-free group and a test substance-containing group by, for example, RT-PCR or an in situ hybridization method using expression of a Hcrt gene as an index. Alternatively, a staining method using an antibody such as a fluorescent immunostaining method using a fluorescent antibody, a method of detecting or measuring orexin which has been released into a culture medium by treatment under suitable stimulation, or orexin which has been accumulated in a cell by an immunological procedure such as ELISA or Western blotting, and a method of reacting the culture supernatant or the cell extract with an orexin-sensitive neuron, a cell which expresses a receptor by introducing an orexin receptor gene such as that used upon isolation of orexin, or a kidney cell or a testis cell which expresses an orexin receptor, and detecting the reaction by an appropriate method can be used.

When proliferation of the orexin neuron is significantly promoted in a test substance-containing group as compared with a test substance-free group, the test substance is a candidate of a drug which acts on regulation of wakefulness-sleep via proliferation (induction) of the orexin neuron. The selected test substance includes not only a so-called agonist or antagonist of Hcrt, but also a substance which can vary the expression amount of these proteins from the nature of the present screening method.

A drug selected by the screening method of the present invention acts on regulation of wakefulness-sleep via proliferation (induction) or functional potentiation of the orexin neuron, and is expected as a candidate therapeutic for a brain dysfunction such as reduction in cognitive or learning capacity, a REM sleep disorder exhibiting fragmentation of REM sleep, particularly a problem of wakefulness-sleep caused by aging or a neurogenic disease accompanied with aging, and further, narcolepsy.

<An Agent and a Kit for Inducing an Orexin Neuron>

The present invention provides an agent for inducing an orexin neuron from a neural progenitor cell or a nerve cell containing N-acetyl-D-mannosamine as an active ingredient.

The present invention also provides a kit for inducing an orexin neuron from a neural progenitor cell or a nerve cell, in which reagents containing (1) N-acetyl-D-mannosamine, and (2) at least one inhibitor selected from the group consisting of a Sirtuin 1 inhibitor and an O-linked β-N-acetylglucosamine transferase inhibitor as active ingredients are accommodated in separate containers.

An active ingredient contained in the inducing agent and the kit of the present invention is as described above in the production method of the present invention. As shown in Examples described later, the orexin neuron inducing action of N-acetyl-D-mannosamine is enhanced by combined use with a Sirt inhibitor or an Ogt inhibitor, and is further enhanced by combined use with a Sirt inhibitor and an Ogt inhibitor.

A reagent contained in the inducing agent and the kit of the present invention may contain an optional ingredient to be added to a medium. Examples of the optional ingredient include, but are not limited to, a solvent, a buffer, and an antiseptic.

<Therapeutic Agent for Narcolepsy or Eating Disorder>

"Narcolepsy" to be the treatment target of the therapeutic agent of the present invention is defined in DSM-IV, and use of The International Classification of Sleep Disorder (ICSD-2) is recommended for the diagnosis thereof. Specifically, the detail is described in the guidelines for the diagnosis and treatment of narcolepsy, formed by the Japanese Society of Sleep Research. In the case of animals including human, it is also possible to conveniently collect cerebrospinal fluid from the animal, and judge narcolepsy by measuring the orexin concentration of the fluid by a conventional method. In the case of human, orexin A in the cerebrospinal fluid is low (less than 110 µg/mL) or below detection limit in narcolepsy patients.

The action mechanism of the therapeutic agent of the present invention is induction of orexin neuron in the living body, particularly in the lateral hypothalamic area. In view of such action mechanism, the therapeutic agent of the present invention is also applicable to, besides narcolepsy, the treatment of eating disorders.

In the present invention, the "eating disorder" is defined in DSM-IV, and largely divided into anorexia nervosa (anorexia) and bulimia nervosa (hyperorexia). Anorexia nervosa is classified into a restricting type and a binge eating/purging type, and bulimia nervosa is classified into a purging type and a nonpurging type. In the present invention, an orexin neuron induction action in the lateral hypothalamic area is particularly expected to improve symptoms of anorexia nervosa.

Whether the therapeutic agent of the present invention is effective for narcolepsy can be confirmed by utilizing a test consisting of plural question items, electroencephalography and polysomnography for measuring plural items including brain wave measurement, which are used for diagnosis, and determining whether the test results after administration have improved as compared to those before administration and whether the polysomnography is approaching normal wave pattern. Alternatively, it can also be confirmed by the shifting of the orexin A concentration of the cerebrospinal fluid toward higher values than that before administration.

Whether the therapeutic agent of the present invention is effective for eating disorder can be judged by a return to normal body weight, and normalization of appetite and food intake behavior.

The therapeutic agent of the present invention can be used as a medicament or food with health claims or food additive by using N-acetyl-D-mannosamine singly, or in the form of tablet, pill, granule, fine granules, powder, pellet, capsule, solution, emulsion, suspension, syrup, troche and the like which are formulated by adding excipients (e.g., lactose, sucrose, starch, cyclodextrin etc.) and, in some cases, flavor, dye, seasoning, stabilizer, preservative and the like. In addition, the therapeutic agent of the present invention can also be used as a reagent for researches.

While the amount of N-acetyl-D-mannosamine contained in the therapeutic agent of the present invention is not particularly limited as long as the effect of the invention is afforded, it is generally 0.0001-100 wt %, preferably 0.001-99.9 wt %.

The present invention also provides a pharmaceutical composition containing an effective amount of N-acetyl-D-mannosamine and a pharmaceutically acceptable carrier, which is used for treating narcolepsy or eating disorder based on the induction of orexin neuron in the living body.

Examples of the pharmaceutically acceptable carrier include, but are not limited to, excipients (e.g., lactose, sucrose, dextrin, hydroxypropylcellulose, polyvinylpyrrolidone etc.), disintegrants (e.g., starch, carboxymethylcellulose etc.), lubricants (e.g., magnesium stearate etc.), surfactants (e.g., sodium lauryl sulfate etc.), solvents (e.g., water, brine, soybean oil etc.), preservatives (e.g., p-hydroxybenzoate etc.) and the like.

While the effective amount of N-acetyl-D-mannosamine is not particularly limited as long as the effect as a medicament is afforded, it is generally 0.0001-99.5 wt %, preferably 0.001-99.0 wt %.

The therapeutic agent or pharmaceutical composition of the present invention can be safely administered orally or parenterally to a mammal (e.g., mouse, rat, rabbit, cat, dog, bovine, horse, monkey, human).

The present invention provides a food added with N-acetyl-D-mannosamine as a therapeutic agent for narcolepsy or eating disorder.

While the "food" in the present invention means food in general, it also includes general foods including what is called health food, and food with health claims such as food for specified health uses, food with nutrient function claims and the like defined by the food with health claims system of the Ministry of Health, Labour and Welfare. Furthermore, supplement, feed and the like are also encompassed in the food of the present invention.

When used for food, N-acetyl-D-mannosamine can also be used by adding to general foods (including what is called health food), for example, bread, confectionery and the like. In addition, N-acetyl-D-mannosamine can be formulated into tablet, pill, granule, fine granules, powder, pellet, capsule, solution, emulsion, suspension, syrup, troche and the like together with an excipient (e.g., lactose, sucrose, starch etc.) and, in some cases, flavor, dye and the like, and used as food with health claims such as food for specified health uses, food with nutrient function claims and the like, or supplement. Moreover, the food of the present invention can also be applied to a feed use, and can be added to a general feed for poultry, domestic animals and the like to allow for ingestion or administration.

When ingested as a food or feed, the daily ingestion frequency and ingestion amount per ingestion of the food or feed are roughly estimated, and the daily ingestion amount is defined, based on which the amount of N-acetyl-D-mannosamine contained in the daily ingestion amount is determined. The content of N-acetyl-D-mannosamine can be determined based on the below-mentioned doses.

The ingestion amount or dose of the therapeutic agent, food or pharmaceutical composition of the present invention varies depending on the age, body weight and health condition of the subject of ingestion or administration, and cannot be determined unconditionally. For example, when the object is prophylaxis or improvement of narcolepsy or maintenance of normal food intake behavior, the form of food is generally employed and, when the object is treatment of narcolepsy or eating disorder or recovery of health, the form of pharmaceutical product or food is generally employed, and 0.1-10 g, preferably 0.2 g-7 g, of N-acetyl-D-mannosamine is preferably ingested by or administered to an adult in one to several portions per day.

The administration method of the medicament (agent or pharmaceutical composition) of the present invention is not particularly limited as long as it is a pathway affording a prophylactic or therapeutic effect on the above-mentioned diseases or disorders. For example, it can be administered by parenteral administration (intravenous administration, intramuscular administration, intratissue direct administration, intranasal administration, intradermal administration, administration into cerebrospinal fluid and the like) or oral administration. Particularly, when the medicament is applied to human, it can be administered intravenously, intramuscularly or orally. Also, the dosage form is not particularly limited, and the medicament can be administered in various administration dosage forms, for example, oral preparation (granule, powder, tablet, sublingual tablet, film coating agent, sublingual film preparation, capsule, syrup, emulsion, suspension and the like), injection, drip infusion, external preparation (preparations for nasal administration, dermal preparation, ointment and the like).

Moreover, the present invention provides use of N-acetyl-D-mannosamine for the production of a medicament for the treatment of narcolepsy or eating disorder. Specifically, the present invention provides a production method of a medicament using N-acetyl-D-mannosamine for the prophylaxis, improvement or treatment of narcolepsy or eating disorder.

As a production method of the medicament of the present invention, a method known per se in the field of pharmaceutical formulation can be used without limitation.

N-acetyl-D-mannosamine including ManNAc is contained in a trace amount in the cells of human as an intermediate, is considered to have no toxicity (e.g., acute toxicity, chronic toxicity, genetic toxicity, reproductive toxicity, cardiotoxicity, drug interaction, carcinogenicity) and to be highly safe for human.

The medicament of the present invention can be used in combination with one or more other drugs for the treatment, prophylaxis, remission or lowering the risk of a disease or condition for which the medicament of the present invention or other drug can exhibit usefulness. In this case, the combination of the drugs is safer or more effective than single use of any drugs. Such other drug can be administered simultaneously or successively with the medicament of the present invention by a pathway and in an amount generally used for the drug. When the medicament of the present invention is used simultaneously with one or more other drugs, a pharmaceutical composition in a unit dosage form containing other such drug and N-acetyl-D-mannosamine is preferable. However, the combination therapy may also include a therapy wherein N-acetyl-D-mannosamine and one or more other drugs are administered in different duplicate schedules. When they are used in combination with one or more other active ingredients, it is also assumed that N-acetyl-D-mannosamine and the aforementioned other active ingredients may each be used in an amount of dose smaller than that for single use thereof. Accordingly, the pharmaceutical composition of the present invention includes one containing one or more other active ingredients in addition to N-acetyl-D-mannosamine. The aforementioned combination includes not only a combination of N-acetyl-D-mannosamine and one other active compound but also a combination thereof with two or more other active compounds.

The weight ratio of N-acetyl-D-mannosamine to the second active ingredient may vary and depends on an effective dose of each component. In general, each effective dose is used. Accordingly, for example, when N-acetyl-D-mannosamine is combined with other drug, the weight ratio of N-acetyl-D-mannosamine to said other drug is generally within the range of about 1000:1 to about 1:1000, preferably about 200:1 to about 1:200. While the combination of N-acetyl-D-mannosamine and other active ingredient is also generally within the aforementioned range, an effective dose of each active ingredient should be used in each case. In such combination, N-acetyl-D-mannosamine and other active drug can be administered individually or together. Furthermore, one factor can be administered before, simultaneously with or after administration of other drug.

The medicament of the present invention can be used in combination with a drug currently used for the treatment of narcolepsy or a drug currently under development as a therapeutic agent for narcolepsy. The medicament of the present invention can be administered in combination with other compounds known in this field to be useful for the treatment of narcolepsy, including Ritalin (methylphenidate), Modiodal (Modafinil), Armodafinil (CEP-10953), Pemoline (Betanamin), Clarithromycin, BF2.649 (Pitolisant), Vigil, PF-03654746, GSK189254, ADK-N05, Flumazenil, orexinA, Sodium Oxybate (Xyrem), APD916, Methylphenidate, NRP104, Pramipexole, Almorexant, caffeine and a combination of these and the like.

The medicament of the present invention can be used in combination with a drug currently used for the treatment of eating disorder (particularly anorexia) or a drug currently under development as a therapeutic agent for eating disorder (particularly anorexia). The medicament of the present invention can be administered in combination with other compounds known in this field to be useful for the treatment of eating disorder (particularly anorexia), including Risperidone, Estrogen/Progesterone, ω-3 fatty acid, Teriparatide, Somatropine, transdermal 17-β estradiol, human growth hormone (genetical recombination), RM-131, Quetiapine, Olanzapine, Methylphenidate, human insulin-like growth factor (genetical recombination: rhIGF-1), Teriparatide, Somatropine, DHEA (Dehydroepiandrosterone, Prasterone), Dronabinol, Ghrelin, Testosterone, Testosterone cypionate, Fluoxetine, Aripiprazole, ERT (Aviane), Norgestimate, Ethinylestradiol, Alprazolam, Atomoxetine, Duloxetine, amino acid, serotonin, hydroxyzine, hydroxyzine HCl, oxytocin and a combination of these and the like.

The medicament of the present invention can be administered in combination with other compounds known in this field to improve the quality of sleep and be useful for the prophylaxis or treatment of sleep disorder, including, for example, sedative, hypnotic, antianxiety drug, anti-histamine, benzodiazepine, barbiturate, cyclopyrrolone, GABA agonist, 5HT-2 antagonists including 5HT-2A antagonist and 5HT-2A/2C antagonist, histamine H3 antagonist, histamine H3 inverse agonist, imidazopyridine, minor tranquilizer, melatonin agonist and antagonist, melatonregic agent, orexin agonist, prokineticin agonist and antagonist, pyrazolopyrimidine, T-type calcium channel antagonist, triazolopyridine, and adinazolam, allobarbital, alonimid, alprazolam, amitriptyline, amobarbital, amoxapine, APD-125, bentazepam, benzoctamine, brotizolam, bupropion, busprione, butabarbital, butalbital, capromorelin, capuride, carbochloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, ramelteon, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, a combination thereof, and the like.

In another embodiment, the medicament of the present invention can be employed for combination with other compounds, which are known in this field, and either individually administered or in the same pharmaceutical compositions, including, but are not limited to (a) PPARγ antagonists such as glitazone (e.g., ciglitazone, darglitazone, englitazone, isaglitazone (MCC-555), pioglitazone, rosiglitazone, troglitazone, tularik, BRL49653, CLX-0921, 5-BTZD), GW-0207, LG-100641, LY-300512 and the like;

(b) biguanides such as metformin and phenformin and the like;

(c) insulin, or insulin analogs such as biota, LP-100, novarapid, insulin detemir, insulin lispro, insulin glargine, insulin zinc suspension (lente and ultralente) and the like, Lys-Pro insulin, GLP-1(73-7) (insulintropin), GLP-1(7-36)-NH$_2$;

(d) sulfonylureas such as acetohexamide, chlorpropamide, diabinese, glibenclamide, glipizide, glyburide, glimepiride, gliclazide, glipentide, gliquidone, glisolamide, tolazamide, tolbutamide and the like;

(e) α-glucosidase inhibitors such as acarbose, adiposine and the like, camiglibose, emiglitate, miglitol, voglibose, pradimicin-Q, salbostatin, CKD-711, MDL-25,637, MDL-73,945, MOR 14 and the like;

(f)

(i) HMG-CoA reductase inhibitors (atorvastatin, itavastatin, fluvastatin, lovastatin, pravastatin, rivastatin, rosuvastatin, simvastatin, and other statins), (ii) bile acid absorbers/scavengers such as colestyramine, colestipol, dialkylaminoalkyl derivatives of a cross-linked dextran and the like, Colst (registered trade mark) and the like,
(iii) nicotinyl alcohol, nicotinic acid, or a salt thereof,
(iv) proliferator-activator receptor α agonists such as fenofibric acid derivatives (gemfibrozil, clofibrate, fenofibrate and benzafibrate) and the like, (v) stanol ester, β-sitosterol, sterol glycosides such as tiqueside and the like, azetidinones such as ezetimibe and the like, and (acylCoA: cholesterolacyl transferase (ACAT)) inhibitors such as avasimibe, and melinamide and the like, (vi) anti-oxidants such as probucol and the like, (vii) vitamin E,
(viii) thyromimetics;
(g) PPARα agonists such as beclofibrate, benzafibrate, ciprofibrate, clofibrate, etofibrate, fenofibrate, gemfibrozil and the like and other fibric acid derivatives such as Atromid (registered trade mark) and Tricor (registered trade mark) and the like, and PPARα agonists described in WO97/36579;
(h) PPARδ agonists;
(i) PPARα/δ agonists such as muraglitazar and the compounds disclosed in U.S. Pat. No. 6,414,002 and the like;
(j)
(l) growth hormone secretagogues, growth hormone secretagogue receptor agonist/antagonists such as NN703, hexarelin, MK-0677, SM-130686, CP-424,391, L-692,429, L-163,255 and the like, (2) protein tyrosine phosphatase-1B (PTP-1B) inhibitors, (3) cannabinoid receptor ligands such as cannabinoid CB1 receptor antagonists and the like or inverse agonists such as rimonabant (Sanofi Synthelabo), AMT-251, SR-14778 and SR141716A (Sanofi Synthelabo), SLV-319 (Solvay), BAY65-2520 (Bayer) and the like, (4) anti-obesity drugs such as fenfluramine, dexfenfluramine, phentermine, sibutramine and the like, (5) AD9677/TAK677 (Dainippon/Takeda), CL-316,243, SB418790, BRL-37344, L-796568, BMS-196085, BRL-35135A, CGP12177A, BTA-243, trecadrine, Zeneca D7114, SR59119A, (6) pancreatic lipase inhibitors such as orlistat (Xenical (registered trade mark), TritonWR1339, RHC80267, lipstatin, tetrahydrolipstatin, tea saponin, diethylumbelliferyl phosphate and the like, (7) neuropeptide Y1 antagonists such as BIBP3226, J-115814, BIB03304, LY-357897, CP-671906, GI-264879A and the like, (8) neuropeptide Y5 antagonists such as GW-569180A, GW-594884A, GW-587081X, GW-548118X, FR226928, FR240662, FR252384, 1229U91, GI-264879A, CGP71683A, LY-377897, PD-160170, SR-120562A, SR-120819A, JCF-104 and the like, (9) melanin-concentrating hormone (MCH) receptor antagonists, (10) melanin-concentrating hormone 1 receptor (MCH1R) antagonists such as T-226296 (Takeda) and the like, (11) melanin-concentrating hormone 2 receptor (MCH2R) agonist/antagonists, (12) serotonin reuptake inhibitors such as fluoxetine, paroxetine, sertraline and the like, (13) melanocortin agonists such as melanotan II and the like, (14) other Mc4r (melanocortin4 receptor) agonists such as CHIR86036 (Chiron), ME-10142, ME-10145 (Melacure), CHIR86036 (Chiron) and the like, (15) 5HT-2 agonist, (16) 5HT2C (serotonin receptor 2C) agonists such as BVT933, DPCA37215, WAY161503, R-1065 and the like, (17) neurotensin antagonists, (18) CCK agonists, (19) CCK-A (secretion promoting effect-A) agonists such as AR-R15849, GI181771, JMV-180, A-71378, A-71623, SR14613 and the like, (20) corticotropin release hormone agonists, (21) histamine receptor-3(H3) modulators, (22) histamine receptor-3(H3) antagonist/inverse agonists such as hioperamide, 3-(1H-imidazol-4-yl)propyl N-(4-pentenyl) carbamate, clobenpropit, iodophenpropit, imoproxifan, GT2394 (Gliatech), 0-[3-(1H-imidazol-4-yl)propanol]-carbamate and the like, (23) PDE (phosphodiesterase) inhibitors such as theophylline, pentoxifylline, zaprinast, sildenafil, amrinone, milrinone, cilostamide, rolipram, cilomilast and the like, (24) phosphodiesterase-3B(PDE3B) inhibitors, (25) NE (norepinephrine) transport inhibitors such as GW320659, despyramine, talsupram, nomifensine and the like, (26) ghrelin receptor antagonists, (27) leptin, including recombinant human leptin (PEG-OB, Hoffman La Roche) and recombinant methionyl human leptin (Amgen) (28) leptin derivatives, (29) BRS3 (bombesin receptor subtype 3) agonists such as [D-Phe6,β-Ala11,Phe13,Nle14]Bn(6-14) and [D-Phe6,Phe13]Bn(6-13)propylamide and those compounds disclosed in Pept. Sci. 2002 August; 8(8): 461-75, (30) CNTF (ciliary neurotrophic factors) such as GI-181771 (Glaxo-SmithKline), SR146131 (Sanofi Synthelabo), butabindide, PD170,292, PD149164 (Pfizer) and the like, (31) CNTF derivatives such as axokine (Regeneron) and the like, (32) monoamine reuptake inhibitors such as sibutramine and the like, (33) UCP-1 (uncoupling protein-1), 2, or 3 activators such as phytanic acid, 4-[(E)-2-(5,6,7,8-tetrahydro-5,5,8,8-tetramethyl-2-naphthalenyl)-1-propenyl]benzoic acid (TTNPB), retinoic acid and the like, (34) thyroid gland hormone β agonists such as KB-2611 (KaroBioBMS) and the like, (35) FAS (fatty acid synthase) inhibitors such as cerulenin and C75 and the like, (36) DGAT1 (diacylglycerol acyltransferase 1) inhibitors, (37) DGAT2 (diacylglycerol acyltransferase 2) inhibitors, (38) ACC2 (acetyl-CoA carboxylase-2) inhibitors, (39) glucocorticoid antagonists, (40) acyl-estrogens such as oleoyl-estrone and the like, disclosed in del Mar-Grasa, M. et al., Obesity Research, 9:202-9 (2001), (41) dipeptidyl peptidase IV (DP-IV) inhibitors such as isoleucine thiazolidide, valine pyrrolidide, NVPDPP728, LAF237, MK-431, P93/01, TSL225, TMC-2A/23/20, FE999011, P9310/K364, VIP0177, SDZ274-444 and the like, (42) dicarboxylate transporter inhibitors, (43) glucose transporter inhibitors, (44)phosphate transporter inhibitors, (45) topiramate (Topimax (registered trade mark)), (46) peptide YY, PYY3-36, peptide YY analogs, derivatives, and fragments such as BIM-43073D, BIM-43004C and the like (Olitvak, D. A. et al., Dig. Dis. Sci. 44(3):643-48(1999)), (47) neuropeptide Y2(NPY2) receptor agonists such as NPY3-36, Nacetyl[Leu(28,31)]NPY24-36, TASP-V, cyclo-(28/32)-Ac-[Lys28-Glu32]-(25-36)-pNPY and the like, (48) neuropeptide Y4(NPY4) agonists such as pancreatic peptide (PP) and the like, and other Y4 agonists such as 1229U91 and the like, (49) cyclooxygenase-2 inhibitors such as etoricoxib, celecoxib, valdecoxib, parecoxib, lumiracoxib, BMS347070, tiracoxib orJTE522, ABT963, CS502, GW406381 and the like, and pharmaceutically acceptable salts thereof, (50) neuropeptideY1 (NPY1) antagonists such as BIBP3226, J-115814, BIB03304, LY-357897, CP-671906, GI-264879A and the like, (51) opioid antagonists such as nalmefene (Revex (registered trade mark)), 3-methoxynaltrexone, naloxone, naltrexone and the like, (52) 11βHSD-1 (11-βhydroxysteroid dehydrogenase type 1) inhibitors such as BVT3498, BVT2733 and the like, (53) aminorex, (54) amphechloral, (55) amphetamine, (56) benzphetamine, (57) chlorphentermine, (58) clobenzorex, (59) chloforex, (60) clominorex, (61) clortermine, (62) cyclexedrine, (63) dextroamphetamine, (64) diphemethoxidine, (65) N-ethylamphetamine, (66) fenbutrazate, (67) fenisorex, (68) fenproporex, (69) fludorex, (70) fluminorex, (71) furfurylmethylamphetamine, (72) levamfetamine, (73) levophacetoperane, (74) mefenorex, (75) metamfepramone, (76) methamphetamine, (77) norpseudoephedrine, (78) pentrex, (79) phendimetrazine, (80) phenmetrazine, (81) picilorex, (82) phytopharm 57, (83) zonisamide and the like.

In another embodiment, the medicament of the present invention can be used in combination with anti-depressant or anti-anxiety drug including norepinephrine reuptake inhibitors (including tertiary amine tricyclic and secondary amine tricyclic), selective serotonin reuptake inhibitors (SSRIs), monoamine oxydase inhibitors (MAOIs), reversible inhibitors of monoamine oxydase (RIMA), serotonin and noradrenaline reuptake inhibitor (SNRIs), corticotropin releasing factor (CRF) antagonists, α-adrenoceptor antagonists, neurokinin-1 receptor antagonists, atypical antidepressants, benzodiazepines, 5-HT1A agonists or antagonists, particularly 5-HT$_{1A}$ partial agonists, corticotropin releasing factor (CRF) antagonists. The particular drug includes amitriptyline, clomipramine, doxepin, imipramine and trimipramine, amoxapine, desipramine, maprotiline, nortriptyline and protriptyline, fluoxetine, fluvoxamine, paroxetine and sertraline, isocarboxazid, phenelzine, tranylcypromine and selegiline, moclobemide, venlafaxine, Aprepitant, bupropion, lithium, nefazodone, trazodone and viloxazine, alprazolam, chlordiazepoxide, clonazepam, clorazepate, diazepam, halazepam, lorazepam, oxazepam and prazepam, buspirone, flesinoxan, gepirone and ipsapirone, and pharmaceutically acceptable salts thereof.

In another embodiment, the medicament of the present invention can be used in combination with anti-Alzheimer's drugs, β-secretase inhibitors, gamma-secretase inhibitors, growth hormone secretagogues, recombinant growth hormone, HMG-CoA reductase inhibitors, NSAID's including ibuprofen, vitamin E, anti-amyloid antibodies, CB-1 receptor antagonists orCB-1 receptor inverse agonists, antibiotics such as doxycycline and rifampin and the like, N-methyl-D-aspartate (NMDA) receptor antagonists such as memantine and the like, cholinesterase inhibitors such as galanthamine, rivastigmine, donepezil, tacrine and the like, growth hormone secretagogues such as ibutamoren, ibutamoren mesylate, capromorelin and the like, histamine H3 antagonists, AMPA agonists, PDE IV inhibitors, GABA A inverse agonists, or neuronal nicotinic agonists.

In another embodiment, the medicament of the present invention can be used in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride and the like, COMT inhibitors such as entacapone and the like, MOA-B inhibitors, antioxidants, Ata adenosine receptor antagonists, cholinergic agonists, NMDA receptor antagonists, serotonin receptor antagonists, dopamine receptor agonists such as alentemol, bromocriptine, fenoldopam, lisuride, naxagolide, pergolide, pramipexole and the like. Dopamine agonist may be in the form of a pharmaceutically acceptable salt thereof, for example, alentemol hydrobromide, bromocriptine mesylate, fenoldopam mesylate, naxagolide hydrochloride, pergolide and mesylate. Lisuride and pramipexol are generally used in a non-salt form.

In another embodiment, the medicament of the present invention can be used in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, or trifluoperazine.

In another embodiment, the medicament of the present invention can be used in combination with an anoretic agent such as aminorex, amphechloral, amphetamine, benzphetamine, chlorphentermine, clobenzorex, cloforex, clominorex, clortermine, cyclexedrin, dexfenfluramine, dextroamphetamine, diethylpropion, diphemethoxidine, N-ethylamphetamine, fenbutrazat, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentrex, phendimetrazine, phenmetrazine, phentermine, phenylpropanolamine, picilorex, sibutramine and the like, selective serotonin reuptake inhibitor (SSRI), halogenated amphetamine derivatives including chlorphentermine, cloforex, clortermine, dexfenfluramine, fenfluramine, picilorex, sibutramine, and pharmaceutically acceptable salts thereof.

A pharmaceutical composition for the administration of N-acetyl-D-mannosamine can be conveniently administered in a unit dosage form, and can be prepared by any method well known in the field of pharmacology. Any method includes a step of blending one or more carriers constituting the aid components and the active ingredient. In general, a pharmaceutical composition is prepared by uniformly and completely mixing a liquid carrier or finely-divided solid carrier or the both with an active ingredient, and forming the product into a desirable dosage form as necessary. A pharmaceutical composition contains an object active compound in an amount sufficient for providing a desired effect on the process or condition of a disease. The term "composition" used in the present specification encompasses a product containing a designated amount of a designated component and any product directly or indirectly obtained from a combination of designated amounts of designated components.

A pharmaceutical composition for oral use can be prepared according to any method known regarding the production of a pharmaceutical composition in this field. Such composition may contain one or more medicaments selected from the group consisting of sweetener, flavor, colorant, and preservative, to provide a preparation having a high pharmaceutical quality and a good taste. A tablet contains an active ingredient mixed with a nontoxic excipient acceptable as a medicament and suitable for the production of tablets. Examples of such excipient include inactive diluents such as calcium carbonate, sodium carbonate, lactose, calcium phosphate, sodium phosphate and the like, granulating agents and disintegrants such as cornstarch, alginic acid and the like, binders such as starch, gelatin, acacia and the like, and lubricants such as magnesium stearate, stearic acid, talc and the like. A tablet may not be coated or may be coated by a technique known to delay disintegration or absorption in the stomach or intestine, whereby a sustained action is provided for a longer time. A composition for oral use can also be provided as a hard gelatin capsule containing an active ingredient mixed with inactive solid diluents, for example, calcium carbonate, calcium phosphate, and kaolin, or a soft gelatin capsule containing an active ingredient mixed with water or an oil medium, for example, peanut oil, liquid paraffin, and olive oil. An aqueous suspension contains an activity material mixed with an excipient suitable for the production of an aqueous suspension. An oily suspension can be prepared by suspending an active ingredient in an appropriate oil. An oil-in-water emulsion can also be adopted. Using dispersible powders and granules suitable for the production of an aqueous suspension by the addition of water, an active ingredient mixed with a dispersing or wetting agent, suspending agent, one or more preservatives is provided. The pharmaceutical composition of the present compound may be in the form of a sterilized injectable aqueous or oily suspension. The medicament of the present invention can also be administered in the form of a suppository for rectal administration. For topical use, cream, ointment, jelly, solution, suspension and the like containing N-acetyl-D-mannosamine can be used. N-acetyl-D-mannosamine can also be prepared for administration by inhalation. N-acetyl-D-mannosamine can also be administered by a transdermal patch by a method known in the field.

<Sleep Disorder Improving Effect by Compounds Represented by Formulas (IIa)-(IIc) and (IIIa)-(IIIc)>

The present inventors clarified various biological activities of ManNAc, found a sleep disorder improving effect of ManNAc, and filed a patent application (e.g., US2011/0212917 A1). The compounds represented by the formulas (IIa)-(IIc) and (IIIa)-(IIIc) (hereinafter to be abbreviated as "compounds (IIa)-(IIc) and (IIIa)-(IIIc)") afford a sleep disorder improving or treating effect equivalent to or higher than that of ManNAc. The "compounds (IIa)-(IIc) and (IIIa)-(IIIc)" may be individually used as a single compound or any combination thereof or these compounds as a whole.

Here, sleep disorders include reduction of sleep volume, reduction of sleep quality and the like, the former manifesting themselves as an increase in the time before falling asleep, and inadequate sleep time due to premature arousal, and the latter manifesting themselves as symptoms such as bedtime shifts, decreased deep sleep (non-REM sleep), sleep interruptions due to premature arousal, naps in active time zones and the like. Sleep disorders occur irrespective of the patient's age; especially the quality of sleep decreases with aging. Diagnoses can be made by a test consisting of a plurality of inquiries, and is established by electroencephalography or by polysomnography, which measures multiple parameters including electroencephalograms. Diagnoses can be classified according to the internationally recognized criteria (The International Classification of Sleep Disorder, ICSD).

In the present invention, "REM sleep" refers to a state of sleep characterized by active brain function and relaxed skeletal muscles. Whether a living organism is in the REM sleep stage can be determined by analyzing electromyograms (EMG) or electroencephalograms (EEG). The REM sleep stage can also be confirmed by observing rapid movements of eyeballs and increased heart rates. On the other hand, "non-REM sleep" refers to a state of sleep characterized by suppressed brain function. Non-REM sleep can also be classified into four categories, from stage 1 (light sleep) to stage 4 (deep sleep), and transition to REM sleep is said to occur in stage 2.

In the present invention, the "REM sleep disorder" refers to a poor or bad condition of a living organism due to a reduction of the REM sleep time associated with aging or other reason. REM sleep disorders can become direct or indirect causal factors of, for example, insomnia, arousal disorders, circadian rhythm aberrations, metabolic or gastrointestinal disorders such as anorexia, weight loss and the like, sensations of fatigue such as generalized lassitude, fatigability and the like, cardiovascular disorders such as hypertension, heart failure and the like. Compounds (IIa)-(IIc) and (IIIa)-(IIIc) can target the prophylaxis, improvement or treatment of such symptoms or conditions.

The compounds (IIa)-(IIc) and (IIIa)-(IIIc) can be administered or taken for the purpose of preventing or improving a disorder selected from the group consisting of the aforementioned sleep disorders (particularly REM sleep disorders, sleep interruptions due to premature arousal), insomnia, arousal disorders, circadian rhythm sleep disorders, delayed sleep phase syndrome and advanced sleep phase syndrome.

For these purposes, the compounds (IIa)-(IIc) and (IIIa)-(IIIc) can be used as a medicament or functional health food or food additive in the form of the compound alone or after being blended with excipients (e.g., lactose, sucrose, starch, cyclodextrin and the like), sometimes further blended with flavors, dyes, seasoning agents, stabilizers, preservatives and the like, into tablets, pills, granules, fine granules, powders, pellets, capsules, solutions, emulsions, suspension, syrups, troches and the like. In addition, the compounds (IIa)-(IIc) and (IIIa)-(IIIc) can also be used as research reagents.

While the amount of the compounds (IIa)-(IIc) and (IIIa)-(IIIc) contained in the pharmaceutical composition or food with health claims or food additive is not particularly limited as long as the effect of the present invention is provided, it is generally 0.0001-100 wt %, preferably 0.001-99.9 wt %.

The present invention also provides a pharmaceutical composition for preventing, improving or treating a sleep disorder, comprising an effective amount of the compounds (IIa)-(IIc) and (IIIa)-(IIIc) and a pharmaceutically acceptable carrier.

Examples of the carrier acceptable as a medicament include, but are not limited to, excipients (e.g., lactose, sucrose, dextrin, hydroxypropylcellulose, polyvinylpyrrolidone and the like), disintegrants (e.g., starch, carboxymethylcellulose and the like), lubricants (e.g., magnesium stearate and the like), surfactants (e.g., sodium lauryl sulfate and the like), solvents (e.g., water, saline, soybean oil and the like), preservatives (e.g., p-hydroxybenzoate and the like) and the like.

While the effective amount of the compounds (IIa)-(IIc) and (IIIa)-(IIIc) are not particularly limited as long as an effect as a medicament is provided, it is generally 0.0001% to 99.5% by weight, preferably 0.001% to 99.0% by weight.

The pharmaceutical composition of the present invention containing the compounds (IIa)-(IIc) and (IIIa)-(IIIc) can be safely administered to mammals (e.g., mice, rats, rabbits, cats, dogs, bovines, horses, monkeys, humans) orally or parenterally.

The compounds (IIa)-(IIc) and (IIIa)-(IIIc) can also be added to food, and provided for improving sleep disorders. The "food" of the present invention here means any food in general, and also includes general foods including what are called health foods, as well as functional health foods such as foods for specified health uses and foods with nutrient function claims, specified in the functional health food system by Japan's Ministry of Health, Labor and Welfare, and nutritional supplements, animal feeds and the like are also encompassed in the food of the present invention.

In food use applications, the compounds (IIa)-(IIc) and (IIIa)-(IIIc) can be used by adding to, for example, general foods (including what are called health foods) such as bread, confectionery and the like. It is also possible to formulate the compounds (IIa)-(IIc) and (IIIa)-(IIIc) along with excipients (e.g., lactose, sucrose, starch and the like), sometimes further with flavors, dyes and the like, into preparations such as tablets, pills, granules, fine granules, powders, pellets, capsules, solutions, emulsions, suspensions, syrups, troches and the like, and use as functional health foods such as foods for specified health uses and foods with nutrient function claims, or nutritional supplements. The food containing the compounds (IIa)-(IIc) and (IIIa)-(IIIc) is also applicable to feed applications, and can be given or administered to poultry, farm animals and the like after adding to ordinary feeds.

When the compounds (IIa)-(IIc) and (IIIa)-(IIIc) are taken as a food or feed, approximate daily intake frequency and intake amount of the food or feed are calculated, the daily intake amount is defined, and the amount of the compounds contained in the daily intake amount of the food or feed is determined. The content of the compounds can be determined based on the doses described below.

The compounds (IIa)-(IIc) and (IIIa)-(IIIc) can also be provided as a commercial package further containing a printed matter bearing an explanation concerning the pharmaceutical composition, stating that the pharmaceutical composition can be used, or should be used, to prevent, improve or treat sleep disorders.

To allow a food containing the compounds (IIa)-(IIc) and (IIIa)-(IIIc) to exhibit the biological action of the compounds effectively, it is preferably used as a food for specified health uses or a food with nutrient function claims. In this case, it is recommended that the product be labeled with indication, "to be used to improve quality of sleep and wake-up", and "well-organize daily activities".

The ingestion or dose of a food or pharmaceutical composition containing the compounds (IIa)-(IIc) and (IIIa)-(IIIc) varies depending on the age, body weight and health status of the subject of ingestion or administration, and cannot be generalized. For example, it is preferable that 0.1 to 10 g, preferably 0.2 g to 7 g, calculated as the compounds (IIa)-(IIc) and (IIIa)-(IIIc), be taken or eaten per day for an adult in one to several portions usually in the form of a food aiming to maintain and enhance health or prevent or improve sleep disorder, and usually in the form of a pharmaceutical product or food for treating sleep disorders or restoring health.

The administration method of the pharmaceutical composition containing the compounds (IIa)-(IIc) and (IIIa)-(IIIc) of the present invention is not particularly limited as long as it is a pathway affording a prophylactic or therapeutic effect on sleep disorders. For example, the pharmaceutical composition can be administered by parenteral administration (intravenous administration, intramuscular administration, direct administration into tissue, intranasal administration, intradermal administration, intramedullary administration and the like) or oral administration. When the pharmaceutical composition is applied to human, in particular, it can be administered by intravenous, intramuscular or oral administration. There is no limitation on the dosage form and it can be administered as various dosage forms, e.g., oral formulations (granules, powders, tablets, capsules, syrups, emulsions, suspensions and the like), injections, drip infusions, external formulations (nasal preparations, transdermal preparations, ointments and the like).

EXAMPLES

The present invention will be explained more specifically by way of examples. The following shows representative examples, and the present invention is not limited to them. However, a variety of applications are possible within the bounds of not departing from the technical idea of the present invention.

Example 1

Induction of Expression of an Orexin Gene (Hcrt) with ManNAc Using a System of Induction of Neural Differentiation from an ES Cell Analysis Using a Stromal Cell-Derived Inducing Activity (SDIA) Differentiation Culture System
Differentiation Culturing Mouse ES cells (J1 strain) which had been maintained in a medium for an ES cell [DMEM (Wako) added with 15% FBS (Biowest), 1 mM sodium pyruvate (Invitrogen), 100 mM β-mercaptoethanol (Invitrogen), 2 mM L-glutamine (Invitrogen), 1 mM non essential amino acid (Invitrogen), 50 U/ml penicillin/50 µg/ml streptomycin (Invitrogen), 2000 U leukemia inhibitory factor (Chemicon, CA)] were seeded on a 10 cm culture dish so that the cell count became $1 \times 10^5$ cells per culture dish on which PA6 stromal cells had been seeded in advance, and differentiation induction was performed in a medium for neural differentiation [Glasgow MEM (Invitrogen) added with 10% KSR (Invitrogen), 100 mM β-mercaptoethanol (Invitrogen), 1 mM non essential amino acid (Invitrogen), 50 U/ml penicillin/50 µg/ml streptomycin (Invitrogen)] for 10 days. On 4th and 7th days of differentiation culturing, the medium was exchanged. In addition, from 4th day of differentiation culturing, 5 nM recombinant human BMP4 (Wako) was added (FIG. 1). On 10th day of differentiation culturing, cells were collected and pelletized by a centrifugation operation to remove the culture medium. Thereafter, the pellets were immediately frozen in liquid nitrogen and stored at −80° C. until use.

REFERENCES

Mizuseki K, Sakamoto T, Watanabe K, Muguruma K, Ikeya M, Nishiyama A, Arakawa A, Suemori H, Nakatsuji N, Kawasaki H, Murakami F, Sasai Y. Generation of neural crest-derived peripheral neurons and floor plate cells from mouse and primate embryonic stem cells. (2003) Proc. Natl. Acad. Sci. USA. 100(10):5828-33.
Expression Analysis by an RT-PCR Method The total RNA was extracted from the collected cells using RNeasy plus Mini Kit (QIAGEN). Then, a reverse transcription reaction was performed in a reaction liquid containing 1 µg of the total RNA, and Oligo (dT) using SuperScript III First Strand Synthesis System (Invitrogen) to synthesize a cDNA.

A PCR reaction was performed on a 10 µl scale, 1 U of LA-Taq DNA Polymerase (Takara) was added to 0.5 µl of a cDNA, 5 µl of 2×GC Buffer I, each 200 µM of dNTP, 1.5 mM $MgCl_2$, and each primer having a final concentration of 0.2 µM, thermal denaturation was performed at 95° C. for 3 minutes, and the reaction was performed under the condition of (30 seconds at 95° C., 30 seconds at 55° C., and 30 seconds at 72° C.)×35 cycles (20 cycles in the case of Actb). The primers used are shown below.

```
Hcrt Forward;
                               (SEQ ID NO: 1)
5'- CTCCAGGCACCATGAACTTT -3'

Hcrt Reverse;
                               (SEQ ID NO: 2)
5'- AGTTCGTAGAGACGGCAGGA -3'
```

-continued

Actb Forward;
(SEQ ID NO: 3)
5'- TTCTACAATGAGCTGCGTGTGG -3'

Actb Reverse;
(SEQ ID NO: 4)
5'- ATGGCTGGGGTGTTGAAGGT -3'

Each PCR product was electrophoresed on a 2% agarose gel, stained with ethidium bromide, and a band was observed by UV irradiation.

Results

Figure 2:
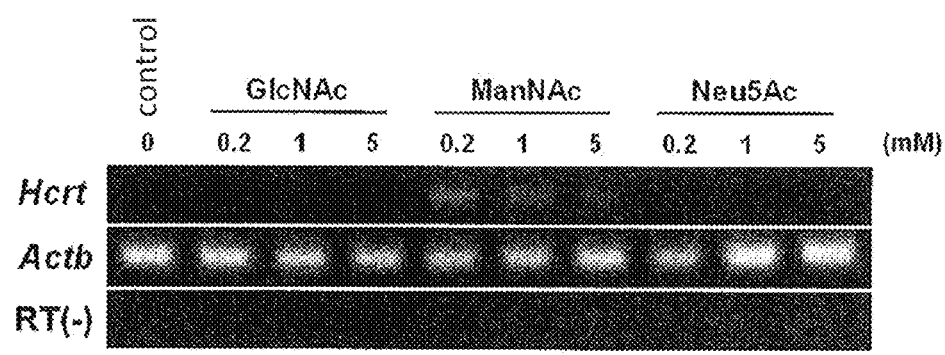
FIG. 2 shows expression of a Hcrt gene in neurally differentiated cells using a medium with GlcNAc, a medium with ManNAc and a medium with Neu5Ac added thereto.

Experiment 1, FIG. 2

From the initiation of differentiation culturing, GlcNAc (N-acetyl-D-glucosamine), ManNAc and Neu5Ac (N-acetylneuraminic acid) were added to a neural differentiation medium so that the concentration became 0.2 and 1.0 mM, and cells were collected on 10th day of differentiation culturing and subjected to RT-PCR. Expression of an orexin gene (Hcrt) was analyzed, and as a result, expression of Hcrt was recognized only in a ManNAc-added section. In addition, a similar effect was obtained also in a human-derived pluripotent stem cell.

Figure 3:
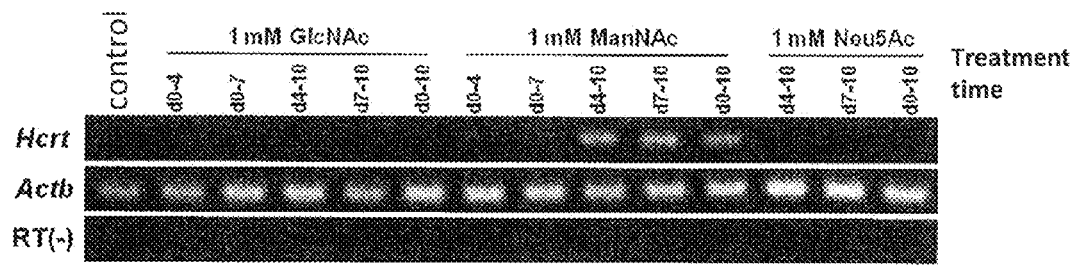
FIG. 3 shows influence of the time for adding GlcNAc, ManNAc and Neu5Ac on expression of a Hcrt gene.

Experiment 2, FIG. 3

Then, GlcNAc, ManNAc and Neu5Ac were added at the concentration of 1.0 mM by changing the time for adding them, and neural differentiation culturing was performed. As a result of analysis by RT-PCR, expression of Hcrt was observed only in a ManNAc-added section at any addition time. In addition, in the 1.0 mM ManNAc-added section, high expression was observed in the section in which ManNAc was added to a medium on and after 7th day of differentiation (ManNAc was added on 4th to 10th days, 7th to 10th days and 0th to 10th days) as compared with other two sections (ManNAc was added on 0th to 4th days and 0th to 7th days).

Example 2

Analysis Using a SFEB/gfCDM*Differentiation Culture System

*: abbreviation of serum-free culture of embryoid body-like aggregates/growth factor-free chemically defined medium
Differentiation Culturing Mouse ES cells (J1 strain) which had been maintained in a medium for an ES cell were seeded on a 96-well low adhering round-bottom culture dish (Nunc) so that the cell count became 10,000 cells per well, and cultured with gfCDM [IMDM/F12 (Invitrogen) added with 5 mg/ml BSA (SIGMA), 450 µM Monothioglycerol (Wako), 1× chemically defined lipid concentrate (Invitrogen), 50 U/ml penicillin/50 µg/ml streptomycin] for 7 days. The cells were cultured in 150 µl of a medium per well. On 7th day of differentiation culturing, the medium was exchanged with a DFK medium [DMEM/F12 (Invitrogen) added with 7 g/l glucose, 10% KSR, 50 U/ml penicillin/50 µg/ml streptomycin], and on 10th day, half the amount of the medium was exchanged with a DFNB medium [7 g/l glucose, 1×N2 (Wako), 1×B27 (Invitrogen)] containing 10 ng/ml CNTF. On 13th day of culturing, cells were detached with 0.05% trypsin/EDTA, seeded on a culture dish (Falcon) which had been treated with poly-D-lysine/laminin so that the cell count became $4.8 \times 10^6$ cells per 10 cm culture dish, and cultured in a DFNB medium containing 10% FBS, 10 ng/ml CNTF, 50 ng/ml BDNF and 50 ng/ml NT3. The medium was exchanged every 3 days. On 25th day of differentiation culturing, cells were collected and pelletized by a centrifugation operation to remove the culture medium. Thereafter, the pellets were immediately frozen in liquid nitrogen, and stored at −80° C. until use.

REFERENCES

Figure 4:
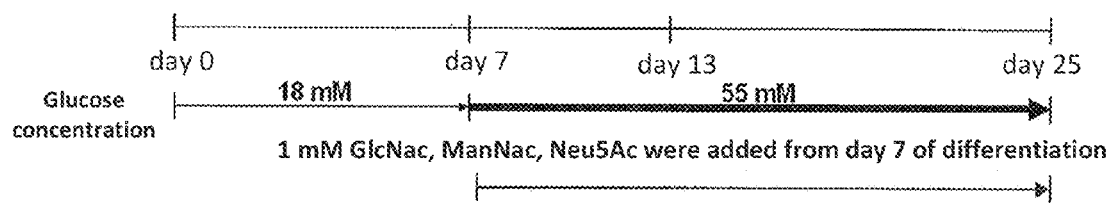
FIG. 4 shows a schedule of induction of neural differentiation by a SFEB/gfCDM method.
Figure 5:
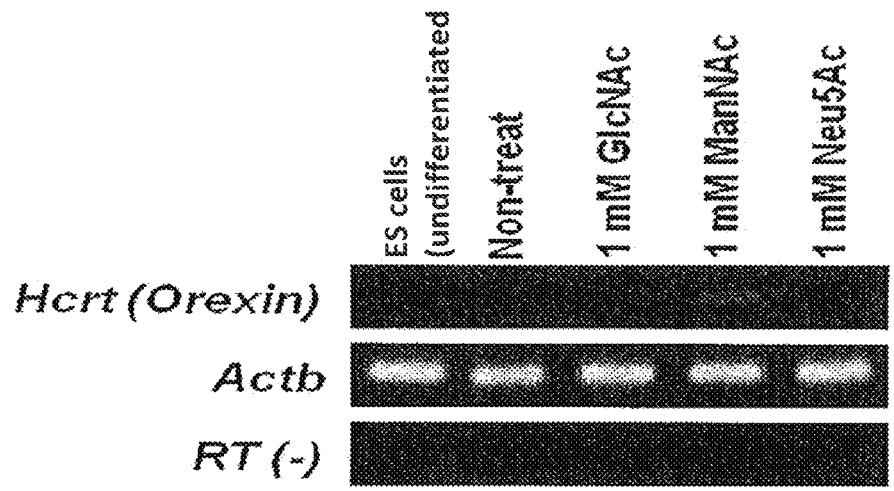
FIG. 5 shows expression of a Hcrt gene in neurally differentiated cells with GlcNAc, ManNAc and Neu5Ac added thereto, which were made by a SFEB/gfCDM method.

Wataya T, Ando S, Muguruma K, Ikeda H, Watanabe K, Eiraku M, Kawada M, Takahashi J, Hashimoto N, Sasai Y. Minimization of exogenous signals in ES cell culture induces rostral hypothalamic differentiation. (2008) Proc. Natl. Acad. Sci. USA., 105(33):11796-801.
Expression Analysis by an RT-PCR Method The analysis was performed by the same method as that of Example 1.
Results (FIGS. 4 and 5)

From 7th day of differentiation culturing, GlcNac, ManNAc and Neu5Ac were added to a medium at the concentration of 1.0 mM, and neural differentiation induction was performed. As a result, expression of Hcrt was recognized in ManNAc and Neu5Ac-added sections. In addition, high expression of Hcrt was observed in a ManNAc-added section as compared with a Neu5Ac-added section.

Example 3

Orexin Inducing Action of ManNAc on a Mouse Fetus-Derived Neurosphere (NSph)

Figure 6:
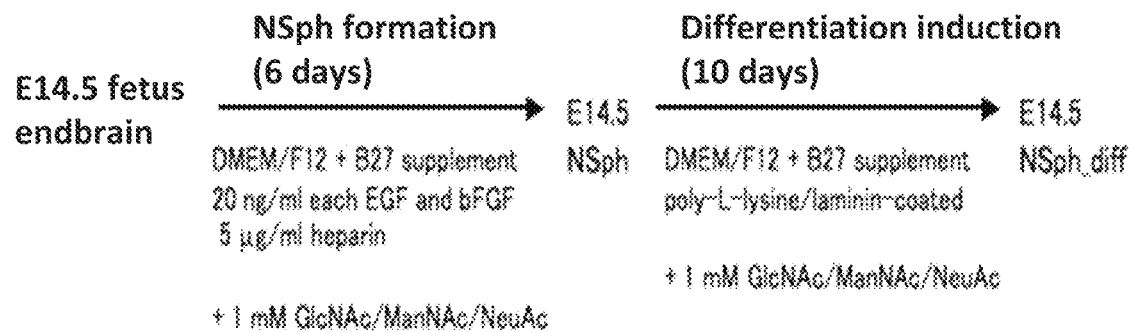
FIG. 6 shows an outline of culture and differentiation induction of a mouse fetus-derived neurosphere (NSph).

Culture of an Endbrain-Derived Neurosphere (NSph) and Differentiation Induction into a Neuron A culture and differentiation induction experiment was performed based on the method of Ciccolini and Svendsen (1998, J Neurosci. 18(19): 7869-80). An outline is shown in FIG. 6. An endbrain was removed from a C57BL/6N mouse fetus having an embryonic age of 14.5 days in ice-cold PBS/0.6% glucose. Dispersion into a single cell was performed by pipetting, and cells were suspended in a medium for NSph [DMEM/F12 (Wako) containing 1×B27 (Invitrogen), 20 ng/ml EGF (Sigma), 20 ng/ml FGF-basic (PEPROTECH), 5 µg/ml heparin (Sigma)] and seeded on a 10 cm petri dish in an amount of $2 \times 10^6$ cells/10 ml. Half the amount of the medium was exchanged 3 days after initiation of culturing, and culturing was performed for another 3 days (total 6 days).

NSph was recovered 6 days after initiation of culturing, and cells were dispersed by pipetting in PBS/0.6% glucose. Cells were collected by centrifugation and suspended in a medium for differentiation induction (not containing EGF, FGF-basic and heparin of a medium for NSph). Cells were seeded in an amount of $4.5 \times 10^5$ cells/7.5 ml on a 6 cm dish which had been coated with poly-L-lysine/laminin (both Sigma) in advance, and differentiation was induced. Half the amount of the medium was exchanged 5 days after initiation of differentiation induction, and culturing was performed for another 5 days (total 10 days). The cells were washed with PBS and then lysed with 0.5 ml TRIzol Reagent (Invitrogen) to be recovered in a 1.5 ml microtube, and stored at −80° C. until use.
Expression Analysis by an RT-PCR Method The total RNA was extracted from the cells which had been lysed with TRIzol Reagent. Using SuperScript III First Strand Synthesis System (Invitrogen), a reverse transcription reaction was performed in 10 μl of a reaction liquid containing 90 ng of the total RNA and Oligo (dT) to synthesize a cDNA. The reaction liquid was diluted 5-fold with 10 mM Tris-HCl (pH 8.0)/0.1 mM EDTA, and used in PCR.

A reaction liquid (20 μl) containing 1×ImmoBuffer, 1.5 mM $MgCl_2$, 0.2 mM each dNTP, 0.2 μM forward primer, 0.2 reverse primer, 1 U of BIOTAQ HS Polymerase (BIOLINE) and 2 of a cDNA was prepared, and after one cycle of 7 minutes at 95° C., PCR was performed under the condition of 24 (Actb)/32 (Prkcz)/36 (Hcrt) cycles of 30 seconds at 94° C., 30 seconds at 62° C., and 30 seconds at 72° C. The primers used are shown below.

```
Actb forward;
                                  (SEQ ID NO: 5)
5'- GACAACGGCTCCGGCATGTGCAAAG -3'

Actb reverse;
                                  (SEQ ID NO: 6)
5'- TTCACGGTTGGCCTTAGGGTTCAG -3'

Prkcz forward;
                                  (SEQ ID NO: 7)
5'- ATGTCTGCTCCTCCAGCAGT -3'

Prkcz reverse;
                                  (SEQ ID NO: 8)
5'- ATATCCTTTCGCTGCACTGG -3'

Hcrt forward;
                                  (SEQ ID NO: 1)
5'- CTCCAGGCACCATGAACTTT -3'

Hcrt reverse;
                                  (SEQ ID NO: 2)
5'- AGTTCGTAGAGACGGCAGGA -3'
```

The PCR product was electrophoresed on a 2% agarose gel, stained with ethidium bromide, and a band was observed by UV irradiation.

Results

At the time when culturing of NSph was initiated, GlcNAc, ManNAc or NeuAc was added so that the concentration became 1 mM, and culturing was performed for 6 days. Subsequently, differentiation induction was performed for 10 days with the added GlcNAc, ManNAc or NeuAc left as it is, and cells were collected (FIG. 6).

Figure 7:
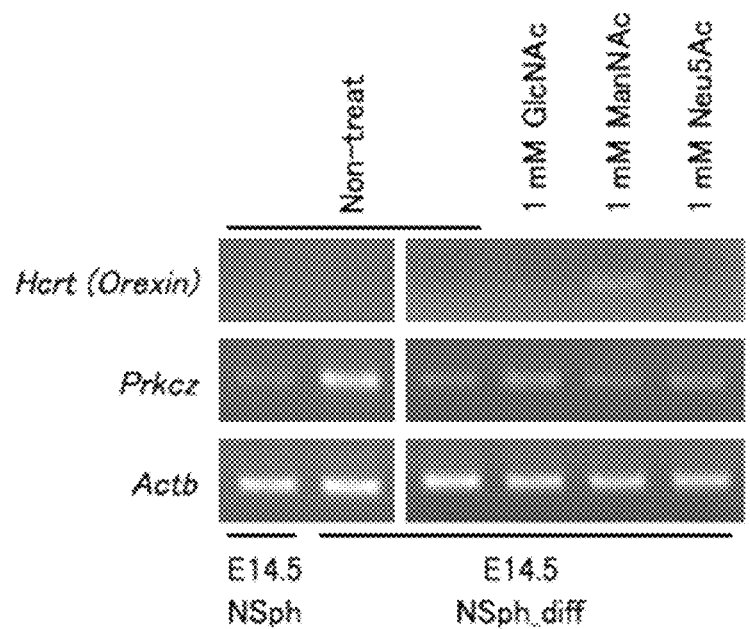
FIG. 7 shows the Hcrt inducing action of ManNAc on a cell differentiated from NSph.

Expression of Hcrt analyzed by RT-PCR was detected only in a 1.0 mM ManNAc-added culture (FIG. 7).

Example 4

Figure 11:
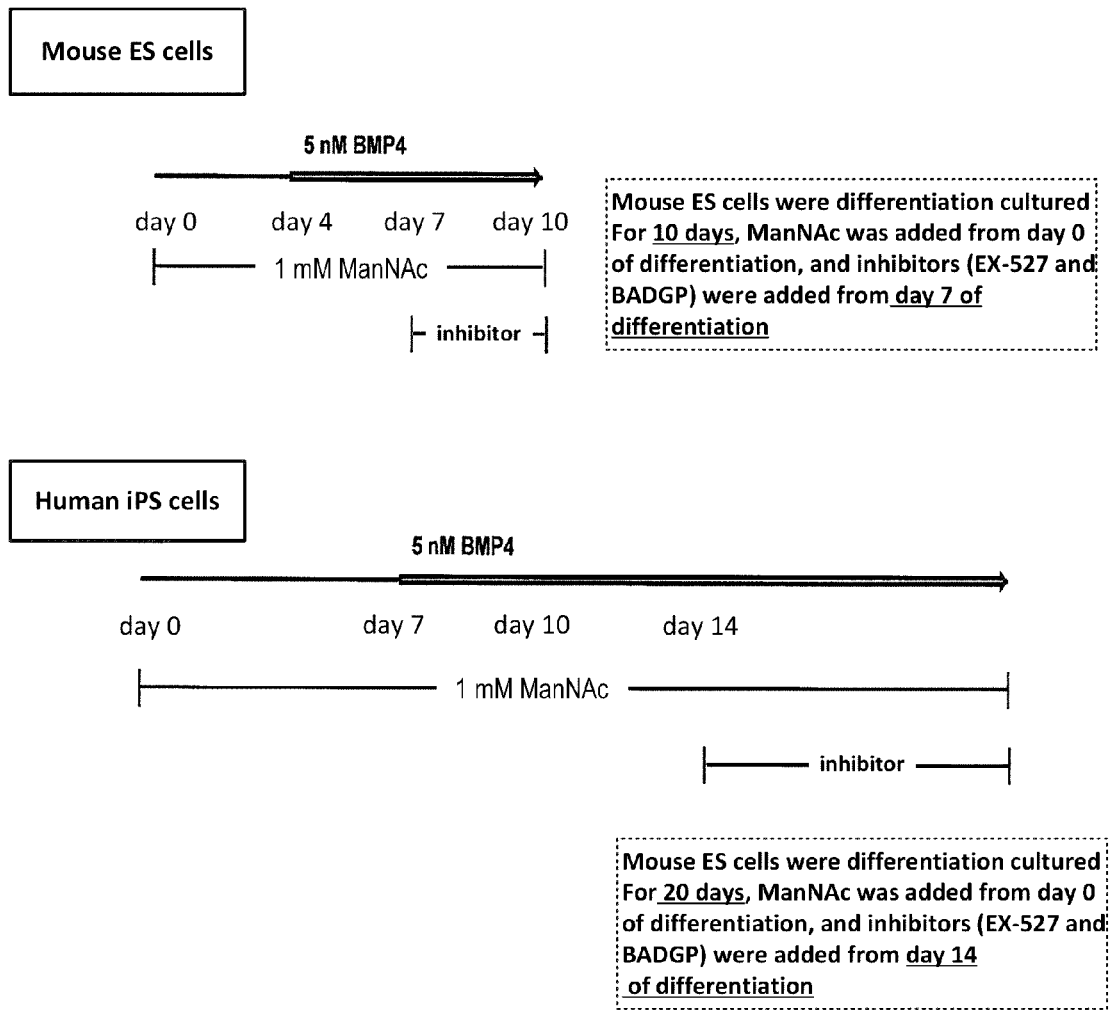
FIG. 11 shows a protocol of inducing differentiation into a nerve cell from a mouse ES cell and a human iPS cell using ManNAc and an inhibitor.

Induction of Expression of an Orexin Gene (Hcrt) with ManNAc as Well as a Sirt Inhibitor and an Ogt Inhibitor Using a System of Induction of Neural Differentiation from a Mouse ES Cell Differentiation Culturing According to the same manner as that described in Example 1, mouse ES cells (J1 strain) were cultured for 10 days for differentiation induction into a nerve cell. A protocol of inducing differentiation into a nerve cell is shown in the upper column of FIG. 11. From the initiation of differentiation culturing (0th day), ManNAc was added to a neural differentiation medium so that the concentration became 1.0 mM, and the medium was exchanged on 4th and 7th days of differentiation culturing. In addition, from 4th day of differentiation culturing, 5 nM recombinant human BMP4 (Wako) was added. On 7th day of differentiation culturing, EX-527 (SIGMA-ALDRICH) was added to a neural differentiation medium so that the concentration became 50 nM or BADGP (SIGMA-ALDRICH) was added to a neural differentiation medium so that the concentration became 1 or 5 mM, and on 10th day of differentiation culturing, cells were collected and subjected to RT-PCR. The conditions of RT-PCR are the same as those of Example 1.

Results

Figure 8:
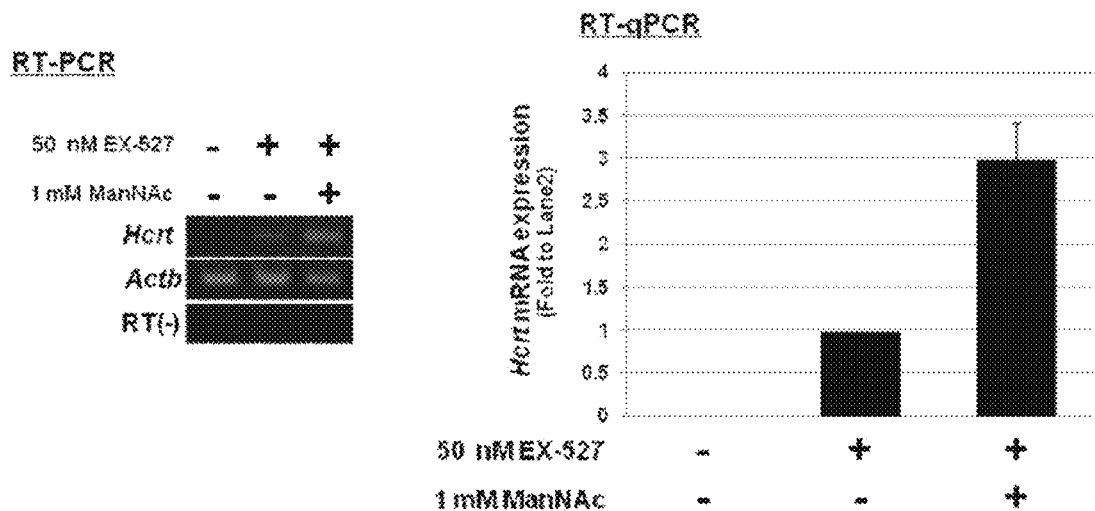
FIG. 8 shows that a Sirt1 inhibitor (EX-527) enhances expression of a Hcrt gene by ManNAc.

Experiment 3, FIG. 8

From the initiation of differentiation culturing, ManNAc was added to a neural differentiation medium so that the concentration became 1.0 mM, on 7th day of differentiation culturing, EX-527 (SIGMA-ALDRICH) was added to a neural differentiation medium so that the concentration became 50 nM, and on 10th day of differentiation culturing, cells were collected and subjected to RT-PCR. Expression of an orexin gene (Hcrt) was analyzed, and as a result, expression of Hcrt was recognized in an EX-527-added section. It was revealed that expression of Hcrt is enhanced by combined use of ManNAc and EX-527.

Figure 9:
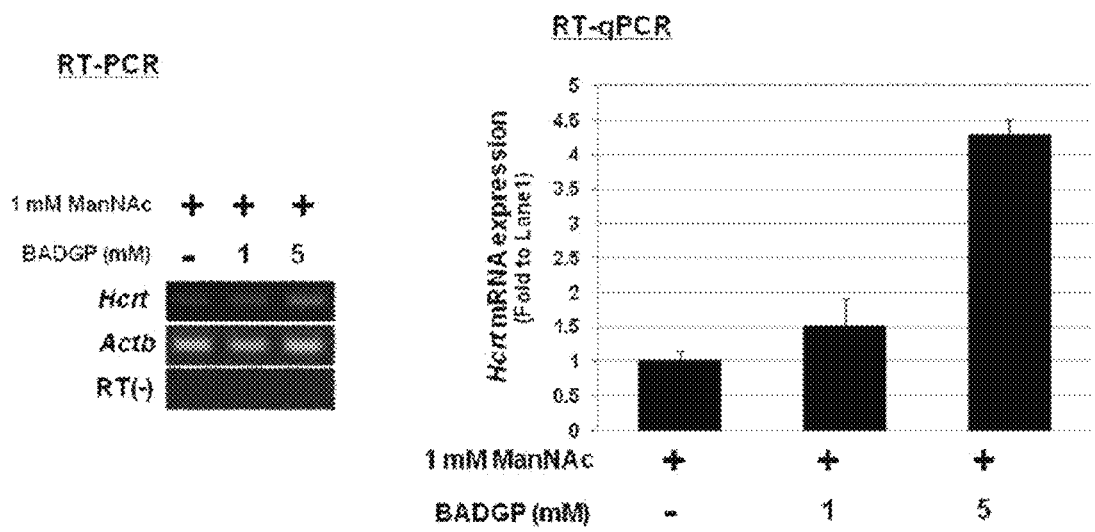
FIG. 9 shows that an Ogt inhibitor (BADGP) enhances expression of a Hcrt gene by ManNAc.

Experiment 4, FIG. 9

Then, from the initiation of differentiation culturing, ManNAc was added to a neural differentiation medium so that the concentration became 1.0 mM, on 7th day of differentiation culturing, BADGP (SIGMA-ALDRICH) was added to a neural differentiation medium so that the concentration became 1 mM or 5 mM, and on 10th day of differentiation culturing, cells were collected and subjected to RT-PCR. Expression of an orexin gene (Hcrt) was analyzed, and as a result, it was revealed that expression of Hcrt which had been recognized in a ManNAc-added section is enhanced by combined use of ManNAc and BADGP. A tendency that expression of Hcrt is increased dependent on the concentration of BADGP was observed.

Example 5

Induction of Expression of an Orexin Gene (Hcrt) with ManNAc as Well as a Sirt Inhibitor and an Ogt Inhibitor Using a System of Induction of Neural Differentiation from a Human iPS Cell Differentiation Culturing A human iPS cell strain 201B7 (HSP0001) was obtained from Riken BioResource Center via National BioResource Project (MEXT, Japan). The human iPS cell was maintained on a feeder layer of a mitomycin C-treated STO/Neo resistant/LIF (SNL) feeder cell in a primate ES medium (ReproCELL) complemented with 5 ng/mL recombinant human bFGF (Wako). The human iPS cell was co-cultured with PA6 for 20 days, for differentiation induction into a nerve with a SIDA and BMP4 system. From 7th day, 5 nM BMP4 was complemented. A detailed protocol of differentiation induction into a nerve cell is shown in the lower column of FIG. 11. From the initiation of differentiation culturing (0th day), ManNAc was added to a neural differentiation medium so that the concentration became 1.0 mM, and on 7th, 10th and 14th days of differentiation culturing, the medium was exchanged. In addition, from 7th day of differentiation culturing, 5 nM recombinant human BMP4 (Wako) was added. On 14th day of differentiation culturing, EX-527 (SIGMA-ALDRICH) was added to a neural differentiation medium so that the concentration became 50 nM, or BADGP (SIGMA-ALDRICH) was added to a neural differentiation medium so that the concentration became 5 mM, and on 20th day of differentiation culturing, cells were collected and subjected to RT-PCR. The conditions of RT-PCR are the same as those of Example 1.

Figure 10:
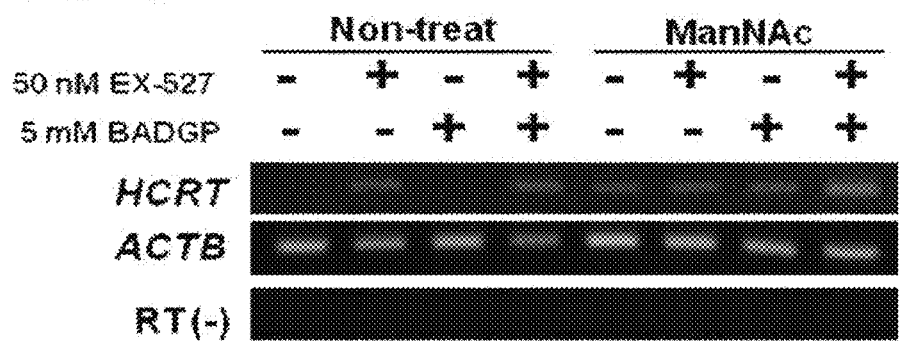
FIG. 10 shows that EX-527 and BADGP enhance expression of a Hcrt gene by ManNAc.
Figure 10:
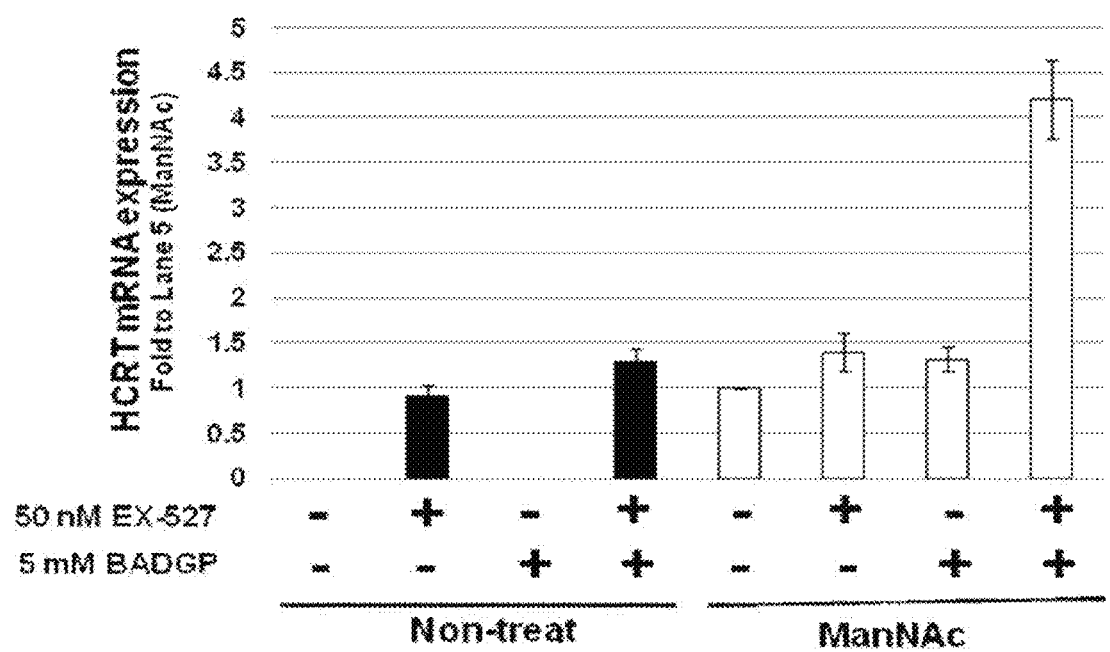

Results (FIG. 10)

Expression of an orexin gene (Hcrt) was analyzed by RT-PCR, and as a result, it was revealed that expression of Hcrt which had been recognized in a ManNAc-added section and an EX-527-added section to the same extent is enhanced by combined use of ManNAc and EX-527, ManNAc and BADGP, or ManNAc, EX-527 and BADGP. Expression of Hcrt was most enhanced by combined use of three kinds of ManNAc, EX-527 and BADGP.

Example 6

Analysis of an Orexin-Positive Cell in a Neurally Differentiated Colony which has been Differentiation-Induced from a Human iPS Cell Cells which had been differentiation-induced on a 4-well culture plate by the method described in Example 5 were fixed with a 4% paraformalin solution, and cellular membrane permeability treatment was performed with a 0.2% Triton-X100 solution. The cells were treated with a 5% bovine serum albumin solution, followed by treatment with a primary antibody (anti-human orexin antibody, anti-human tubulin III antibody) at 4° C. overnight. After a reaction with a secondary labeled antibody (Alex-Fluor 488-labeled donkey anti-goat antibody, Alexa-Fluor 594-labeled rabbit anti-mouse antibody), a nuclear DNA was stained with DAPI. Fluorescence was observed with a fluorescent microscope, and the ratio of orexin-positive cells in a neurally differentiated colony, in which a reaction with an orexin antibody had been recognized, was measured.

As a result, 4.9% of cells became orexin-positive in a ManNAc treatment section, 6.1% of cells became orexin-positive in a ManNAc and EX-527 treatment section, 7.0% of cells became orexin-positive in a ManNAc and BADGP treatment section, and 18.7% of cells became orexin-positive in a ManNAc, EX-527 and BADGP simultaneous treatment section. It was revealed that differentiation of an orexin neuron was remarkably enhanced by a combination of ManNAc and a Sirtuin inhibitor and/or an OGT inhibitor.

Example 7

Increase in Orexin Neuron In Vivo

<ManNAc Administration Conditions>
ManNAc was dissolved in drinking water, and the drinking water with a concentration of 5 mg/ml was administered to old mouse (C57BL/6, male) by allowing free access to water for 8 weeks in total from 53-week-old to 61-week-old. After completion of the administration, the aforementioned mouse was immediately perfusion fixed and subjected to in situ hybridization method. As a control group, ManNAc non-administration old mouse (61-week-old at the time point of fixing) and young mouse (10-week-old at the time point of fixing) were used.

<Detection of Orexin Gene Expression by In Situ Hybridization Method>
Each three mice of ManNAc administration and control groups were anesthetized with Nembutal, and perfusion fixed with formamide fixative (Genostaff). The brain was removed, embedded in paraffin, and 6 μm-thick sections were prepared in the sagittal section direction. The sections were stained with hematoxylin-eosin every 10 sections, and the position of the sections was identified according to the mouse brain atlas (Paxinos G, Franklin K B J. The mouse brain in stereotaxic coordinates. 2nd edition, Academic Press, 2001), and the sections containing the lateral hypothalamic area were subjected to an in situ hybridization method. After deparaffinization treatment with xylene, the sections were rehydrated stepwise with ethanol and PBS. The sections were fixed with 4% para-formaldehyde/PBS for 15 min, and washed with PBS. Then, the sections were treated with 8 g/ml Proteinase K/PBS at 37° C. for 30 min, washed with PBS, re-fixed with 4% para-formaldehyde/PBS for 15 min, washed with PBS, treated with 0.2N HCl for 10 min, and washed with PBS. The sections were treated with 0.1M triethanolamine hydrochloride/0.25% acetic anhydride for 10 min, and washed with PBS. The sections were stepwisely dehydrated with ethanol, and hybridized to RNA probe diluted to 300 ng/ml with Probe Diluent (Genostaff) at 60° C. for 16 hr. As for the probe, a partial sequence of orexin gene:

(SEQ ID NO: 9)
cgtgttcctgccgtctctacgaactgttgcacggagctggcaacca cgctgcgggtatcctgactctgggaaagcggcggcctggacctcca ggcctccagggacggctgcagcgcctccttcaggccaacggtaacc acgcagctggcatcctgaccatgggccgccgcgcaggcgcagagct agagccacatccctgctctggtcgcggctgtccgaccgtaactacc accgctttagcacccgggggagggtccggagtctgaacccatcttc tatccttgtcctgatccaaacttcccctctgctc was cloned into a pGEM-1 Easy vector (Promega) and, using the plasmid as a template and DIG RNA Labeling Mix (Roche), a digoxygenin-labeled RNA probe was produced. After hybridization, the sections were washed with 5×HybriWash (Genostaff) at 60° C. for 20 min. Then, a RNase treatment was performed for 30 min in 50 μg/ml RNaseA, 10 mM Tris-HCl (pH 8.0), 1M NaCl, and 1 mM EDTA solution at 37° C. The sections were washed twice with 2×HybriWash at 60° C. for 20 min, twice with 0.2×HybriWash at 60° C. for 20 min, and once with TEST (0.1% Tween20/TBS). After a blocking treatment with a 0.5% blocking reagent (Roche)/TBST for 30 min, the sections were incubated in anti-DIG AP conjugate (Roche), which had been 1000-fold diluted with TEST, at room temperature for 2 hr. After washing twice with TEST, they were incubated in 100 mM NaCl, 50 mM MgCl$_2$, 0.1% Tween20, 100 mM Tris-HCl (pH 9.5) solution. A color developing reaction was performed using NBT/BCIP (Sigma) overnight, and the sections were washed with PBS. The stained sections were counter stained with Kernechtrot (MUTO PURE CHEMICALS), and enclosed with Malinol (MUTO PURE CHEMICALS). The cells that expressed orexin gene were counted and the average of three animals and the standard error were determined.

Experiment Results

Figure 12:
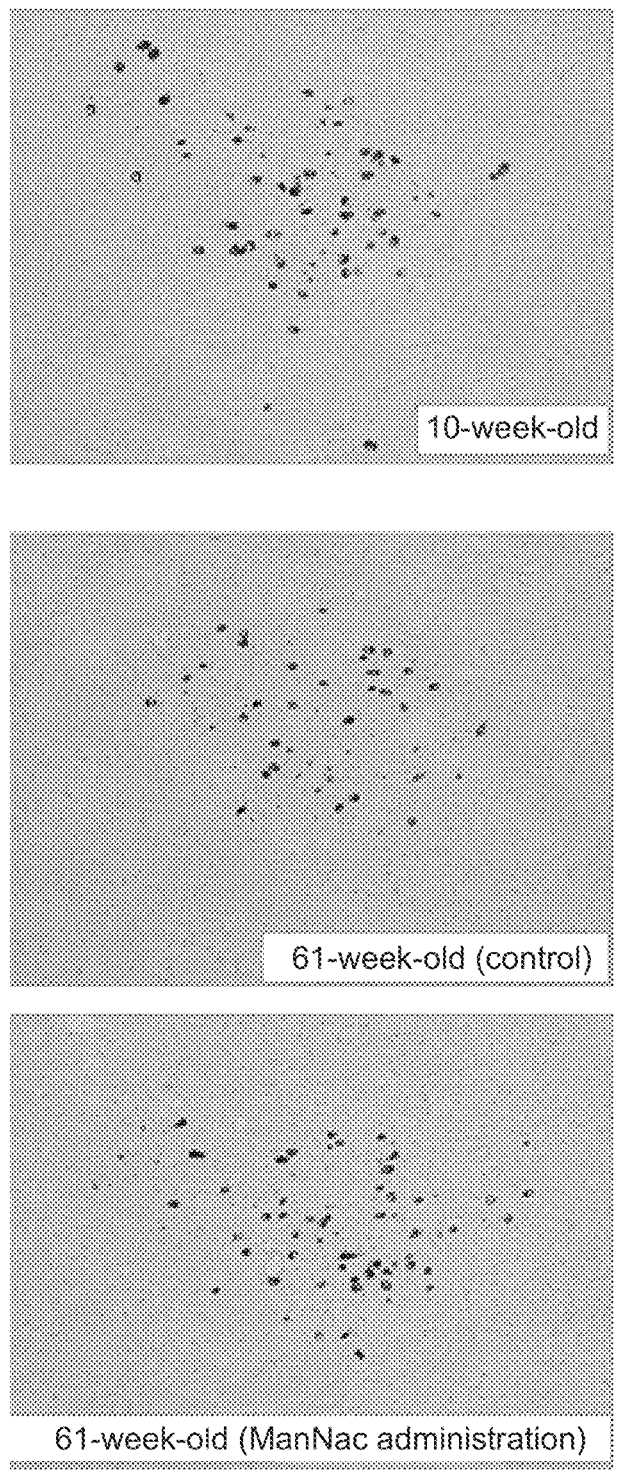
FIG. 12 shows expression states of orexin gene in the lateral hypothalamic area of young mouse, old mouse and old mouse administered with ManNAc.
Figure 12:
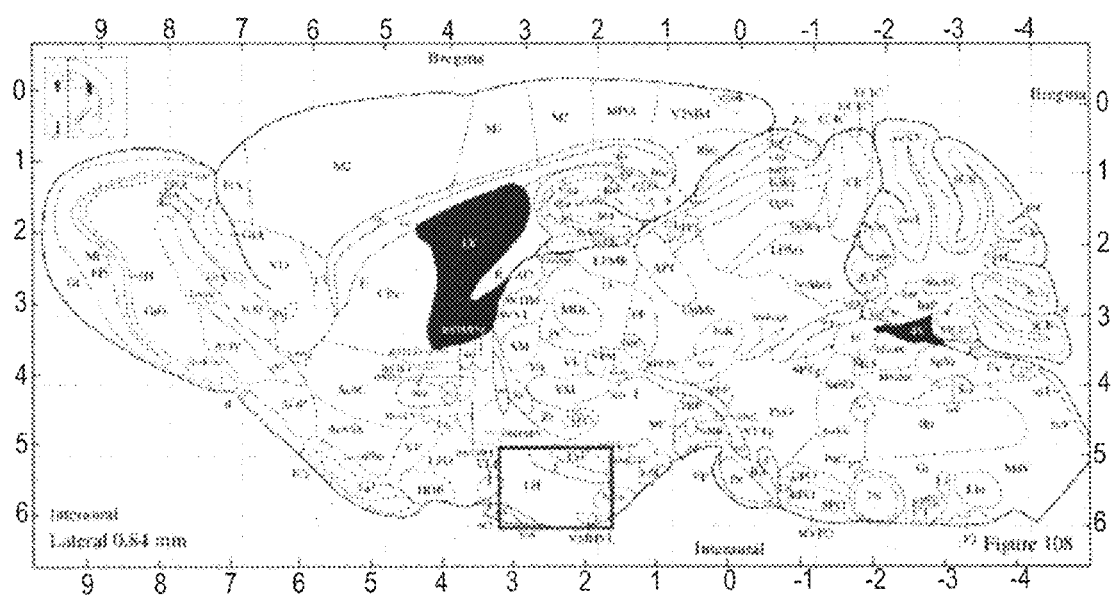
Figure 12:
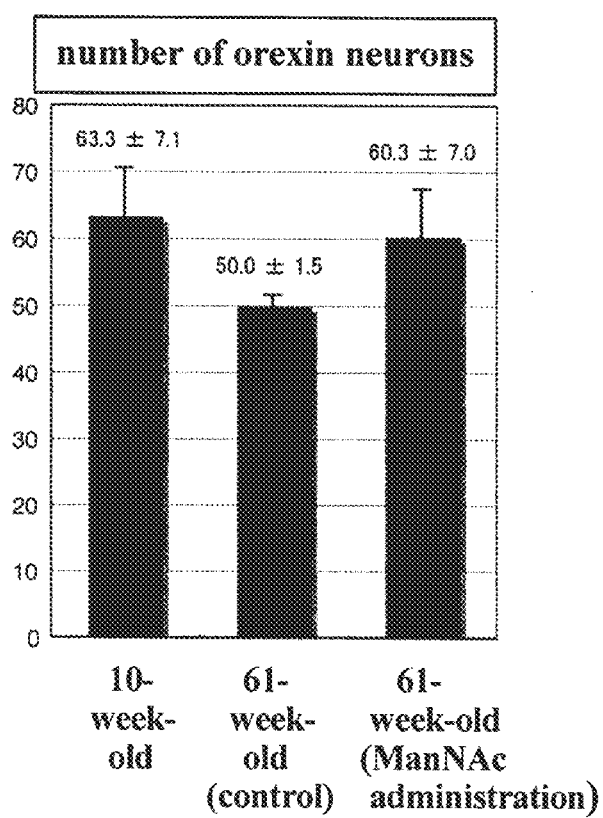

The results are shown in FIG. 12. Orexin gene-expressing cells (orexin neuron) were confirmed in the lateral hypothalamic area, and the number decreased in the non-administration old mouse as compared to the young mouse. On the other hand, the orexin neuron increased in the old mouse administered with ManNAc as compared to the non-administration group.

INDUSTRIAL APPLICABILITY

Using an orexin neuron produced using ManNAc (including derivative thereof, precursor thereof and prodrug thereof), or a combination of ManNAc and a Sirt inhibitor and/or an Ogt inhibitor, a new drug therapy and a drug screening can be provided. The present invention can also contribute to regenerative medicine aiming at recovery of the orexin neuron.

According to the present invention, there are provided medicines, foods and the like containing N-acetyl-D-mannosamine as an active ingredient. By ingestion or consumption of medicines or foods of the present invention, narcolepsy or eating disorder can be prevented, improved or treated based on the orexin neuron induction in vivo.

---

The invention claimed is:

1. A method for inducing an orexin neuron, comprising a step of administering, as an active ingredient, an effective amount of N-acetyl-D-mannosamine to a subject in need thereof, or having, as an active ingredient, an effective amount of N-acetyl-D-mannosamine taken by a subject in need thereof, wherein the N-acetyl-D-mannosamine is selected from the group consisting of

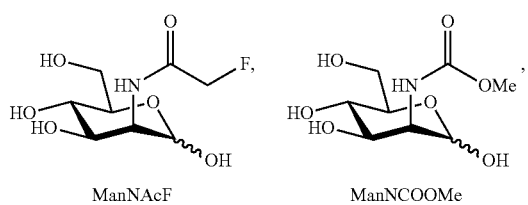

ManNAcF    ManNCOOMe

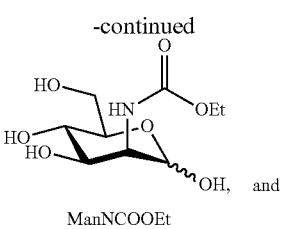

ManNCOOEt salts thereof, whereby the orexin neuron is induced in the lateral hypothalamic area of the subject.

2. A method for treating narcolepsy or eating disorder based on induction of an orexin neuron in vivo, comprising a step of administering, as an active ingredient, an effective amount of N-acetyl-D-mannosamine to a subject in need thereof, wherein the N-acetyl-D-mannosamine is selected from the group consisting of 5S-ManNAcF, and salts thereof, whereby the orexin neuron is induced in the lateral hypothalamic area of the subject and the narcolepsy or the eating disorder is treated in the subject.

3. The method of claim 2, wherein the narcolepsy is treated.

4. The method of claim 2, wherein the eating disorder is treated.

5. The method of claim 4, wherein the eating disorder is anorexia.

6. A method for inducing an orexin neuron, comprising a step of administering, as an active ingredient, an effective amount of N-acetyl-D-mannosamine to a subject in need thereof, or having, as an active ingredient, an effective amount of N-acetyl-D-mannosamine taken by a subject in need thereof, wherein the N-acetyl-D-mannosamine is selected from the group consisting of 5S-ManNAcF, and salts thereof, whereby the orexin neuron is induced in the lateral hypothalamic area of the subject.

7. The method of claim 1, wherein the N-acetyl-D-mannosamine is ManNAcF or a salt thereof.

8. The method of claim 1, wherein the N-acetyl-D-mannosamine is ManNCOOMe or a salt thereof.

9. The method of claim 1, wherein the N-acetyl-D-mannosamine is ManNCOOEt or a salt thereof.

\* \* \* \* \*